(12) United States Patent
Hattori

(10) Patent No.: US 9,233,991 B2
(45) Date of Patent: Jan. 12, 2016

(54) SYMMETRIC HYPERBRANCHED SILICONE-MODIFIED POLYMERIZABLE COMPOUND AND MODULARIZED MANUFACTURING METHOD THEREOF

(71) Applicant: SHIN-ETSU CHEMICAL CO., LTD., Tokyo (JP)

(72) Inventor: Hatsuhiko Hattori, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/198,033

(22) Filed: Mar. 5, 2014

(65) Prior Publication Data

US 2014/0275599 A1 Sep. 18, 2014

(30) Foreign Application Priority Data

Mar. 15, 2013 (JP) .................................. 2013-053378
Dec. 25, 2013 (JP) .................................. 2013-266503

(51) Int. Cl.
*C07F 7/18* (2006.01)
*C07F 7/08* (2006.01)

(52) U.S. Cl.
CPC ................. *C07F 7/18* (2013.01); *C07F 7/0854* (2013.01)

(58) Field of Classification Search
USPC ......................................... 556/439, 443, 444
See application file for complete search history.

(56) References Cited

U.S. PATENT DOCUMENTS

| 6,184,407 | B1 | 2/2001 | Yoshitake et al. |
| 6,306,992 | B1 | 10/2001 | Yoshitake et al. |

| 2003/0019209 | A1 | 1/2003 | Tsuruga et al. |
| 2006/0018935 | A1 | 1/2006 | Nishijima et al. |
| 2007/0275255 | A1* | 11/2007 | Ooms et al. ................... 428/447 |

FOREIGN PATENT DOCUMENTS

| JP | A-06-228167 | 8/1994 |
| JP | B2-4236342 | 3/2009 |
| JP | B2-4270607 | 6/2009 |
| JP | B2-4664062 | 4/2011 |
| JP | B2-4681881 | 5/2011 |
| WO | WO 02/055888 A1 | 7/2002 |

OTHER PUBLICATIONS

Nemoto et al., "An Efficient and Practical Method for the Preparation of a Branched Oligoglycerol with Acetonide Protection Groups," *Chemistry Letters*, Jul. 3, 2010, pp. 856-857, vol. 39.
Extended Search Report issued in European Patent Application No. 14000889.7 dated Jun. 20, 2014.

* cited by examiner

*Primary Examiner* — Sudhakar Katakam
*Assistant Examiner* — Pancham Bakshi
(74) *Attorney, Agent, or Firm* — Oliff PLC

(57) ABSTRACT

The invention provides a symmetric hyperbranched silicone-modified polymerizable compound comprises a compound represented by the general formula (1). There can be provided a symmetric hyperbranched silicone-modified polymerizable compound having a structure with chemically high flexibility at the branched chain, having good reactivity of the polymerizable functional group, and having a branched structure which is positionally and sterically symmetric and pure than the conventional ones.

$$(R^A R^B)_2 CHOR^C_c R^D \qquad (1)$$

wherein $R^A$ represents a monovalent linear, branched or cyclic siloxane chain; $R^B$ represents —$CH_2CR^{b1}R^{b2}(CR^{b3}R^{b4})_{n1}OCH_2$—; $R^C$ represents a divalent linking group; "c" represents 0 or 1; and $R^D$ represents an unsaturated polymerizable functional group.

18 Claims, No Drawings

SYMMETRIC HYPERBRANCHED SILICONE-MODIFIED POLYMERIZABLE COMPOUND AND MODULARIZED MANUFACTURING METHOD THEREOF

BACKGROUND OF THE INVENTION

1. Field of the Invention

The present invention relates to a symmetric hyperbranched silicone-modified polymerizable compound having a siloxane chain, a modularized manufacturing method of the polymerizable compound, and a silicone-modified composition using the polymerizable compound.

2. Description of the Related Art

It has been disclosed that a molecule (carbodendrimer) containing a siloxane structure having regularly branched structures has low viscosity as compared with the conventional linear siloxane having the same number of the silicon atoms, and gives an excellent material as mold releasing agent, lubricant, resin modifier or cross-linking agent (Patent Document 1). Further, a siloxane dendrimer of a polymerizable compound in which a branched siloxane utilizing its features is grafted has been developed (Patent Document 2). However, the siloxane having such a structure has short branched chains and is chemical structurally brittle, so that it is poor in flexibility as a dendrimer. Also, effects of steric hindrance appears accompanied by becoming the grafted branched chain large (generation increases), and reactivity of the polymerizable functional group becomes insufficient, so that commercialization has not been done in the third generation in which the branch is three units in one side chain.

Due to the problems as mentioned above, it has been developed a method in which a siloxane chain is tried to introduce into an allyl ether compound ($CH_2$=$CHCH_2OR$) by hydrosilylation, but it has been known that among the olefins of the allyl ether compound, 10 to 20% thereof is internally rearranged to form a 1-propenyl ether product ($CH_3CH$=$CHOR$), which is a main by-product. Further, it has also been known when the above 1-propenyl ether is hydrolyzed by moisture, etc., in the air, propion aldehyde is generated, which causes bad smell in the final product, etc. To solve the above-mentioned problem of the bad smell, it has been disclosed a method in which a vinyl ether group in the 1-propenyl ether is reduced to propyl ether ($CH_3CH_2CH_2OR$) by hydrogenation reaction using a hydrogen gas under pressure in an autoclave, whereby chemical decomposition thereof is prevented to avoid occurrence of the bad smell (Patent Document 3). Further, there is a problem that the decomposed aldehyde and alcohol are reacted to form acetal in some cases, and the acetal is not reacted by the hydrogenation reaction but gradually decomposes by moisture or acid, which continues to emit the bad smell from the product. To solve the above problem, it has been disclosed a method in which a solid acid is used at the hydrogenation reaction, which can prevent from generating a substance which emits the bad smell (Patent Document 4), and a method in which the generated propion aldehyde is acetalized ($CH_3CH_2CH(OR')_2$) by lower alcohol (R'OH) to make the compound which emits the bad smell a compound having a low boiling point, which is removed by distillation (Patent Document 5). However, these methods are measures for the purposes of suppressing occurrence of the bad smell component or removing the same, whereby they are not the method that basically suppresses the occurrence of the internally rearranged product at the time of the reaction.

On the other hand, it has been known that it is possible to reduce an amount of an internally rearranged product of olefin by using β-methallyl alcohol which is 2-methyl-2-propen-1-ol at the time of the hydrosilylation reaction. However, there are problems that isobutyl aldehyde formed with a minute amount emits an unpleasant odor, and the β-methallyl alcohol used as a raw material is significantly expensive as compared with the allyl alcohol.

Therefore, a branched type siloxane with good purity can be difficulty synthesized from a branched compound containing an ether bond having flexibility due to the problem of the above-mentioned internal rearrangement, and when a silicone is tried to introduce into a branched compound having allyl groups, if internal rearrangement of a by-product is generated in the hydrosilylation reaction, a product one of which is symmetric to the silicone chain cannot be obtained. When an attempt is made to apply the product to use for pharmaceuticals, medical devices or foods, an asymmetric branched compound markedly affected on the effectiveness of the physiological activity due to the formation of diastereomers. Further, it has been known that it is extremely difficult in synthetic chemistry to introduce a branched structure which is positionally and sterically pure and symmetric.

PRIOR ART REFERENCES

Patent Documents

Patent Document 1: Japanese Patent No. 4270607
Patent Document 2: Japanese Patent No. 4236342
Patent Document 3: International Patent Laid-Open Publication No. 02/055888
Patent Document 4: Japanese Patent No. 4681881
Patent Document 5: Japanese Patent No. 4664062

SUMMARY OF THE INVENTION

The present invention has been done in view of the above circumstance and an object thereof is to provide a symmetric hyperbranched silicone-modified polymerizable compound having a structure with chemically high flexibility at the branched portion, having good reactivity of the polymerizable functional group, and having a branched structure which is positionally and sterically symmetric and pure than the conventional ones.

To accomplish the above-mentioned objects, the present invention is to provide a symmetric hyperbranched silicone-modified polymerizable compound containing the compound represented by the following formula (1):

$$(R^A R^B)_2 CHOR^C_c R^D \qquad (1)$$

wherein $R^A$ represents a monovalent linear, branched or cyclic siloxane chain; $R^B$ represents —$CH_2CR^{b1}R^{b2}(CR^{b3}R^{b4})_{n1}OCH_2$—; wherein $R^{b1}$, $R^{b2}$, $R^{b3}$ and $R^{b4}$ each may be the same or different, and each represent a hydrogen atom or a divalent hydrocarbonylene methylene ether group which is a linear, branched or cyclic hydrocarbon group having 1 to 10 carbon atoms, each of which may be bonded; "n1" represents an integer selected from 0 to 10; $R^C$ represents a divalent linking group; "c" represents 0 or 1; and $R^D$ represents an unsaturated polymerizable functional group.

When such a symmetric hyperbranched silicone-modified polymerizable compound is employed, by introducing a glycerin structure having an ether group which is chemically high flexibility into the branched chain, it is possible to obtain a compound having flexibility as a whole molecule, further having good reactivity of the polymerizable functional group, and having a branched structure which is positionally and sterically symmetric and pure than the conventional ones.

Among these, in the divalent hydrocarbonylene methylene ether group represented by $R^B$ of the above-mentioned formula (1), it is preferred that "n1" represents an integer selected from 1 to 10, and when "n1" represents 1, $R^{b1}$ represents a hydrocarbon group having 1 to 10 carbon atoms and $R^{b2}$ represents a hydrogen atom.

By introducing such a divalent hydrocarbonylene methylene ether group, it is possible to obtain a symmetric hyperbranched silicone-modified polymerizable compound having good reactivity of the polymerizable functional group, and having a branched structure which is positionally and sterically symmetric and pure.

It is also preferred that the divalent linking group represented by $R^C$ of the above-mentioned formula (1) is a linking group selected from divalent linking groups represented by —$XR^Y_yR^ZO$—, —$XR^Y_yCR^{Z'}R^{Z''}O$—, and oligoalkyleneoxy group having 2 to 10 carbon atoms and a repeating unit with an integer of 1 to 10;
wherein X represents any one selected from —$CH_2$—, —$C(=O)$—, and —$C(=S)$—, $R^Y$ represents a divalent functional group containing 0 or 1 atom selected from nitrogen atom, oxygen atom, sulfur atom, and carbon atom, $R^Z$ represents a linear, branched or cyclic alkylene group having 2 to 10 carbon atoms which may be substituted by oxygen atom, "y" represents an integer selected from 0 or 1, and $R^{Z'}$ and $R^{Z''}$ each represent an alkyl group having 1 to 10 carbon atoms.

By introducing such a divalent linking group, it is possible to obtain a symmetric hyperbranched silicone-modified polymerizable compound having more flexibility.

The present invention also provides a modularized manufacturing method which is a manufacturing method of the symmetric hyperbranched silicone-modified polymerizable compound, which comprises
reacting the compound represented by the above-mentioned formula (1) with an intermediate represented by the following formula (2) and a compound having an unsaturated polymerizable functional group:

$$(R^AR^B)_2CHOH \tag{2}$$

wherein $R^A$ and $R^B$ have the same meanings as defined above.

When such a modularized manufacturing method is employed, it is possible to manufacture a symmetric hyperbranched silicone-modified polymerizable compound having a branched structure which is positionally and sterically symmetric and pure than the conventional ones.

At this time, the intermediate represented by the above-mentioned formula (2) is preferably manufactured by subjecting a compound represented by the following formula (3) and a compound represented by the following formula (4) to hydrosilylation reaction:

$$R^{A'} \tag{3}$$

wherein $R^{A'}$ represents a linear, branched or cyclic siloxane having one reactive hydrogen in the molecule, hereinafter sometimes abbreviated to as H-siloxane.

$$R^{B'}_2CHOH \tag{4}$$

wherein $R^{B'}$ represents a monovalent hydrocarbonylene methylene ether group represented by $CH_2=CR^{b1}(CR^{b3}R^{b4})_{n1'}OCH_2$— which has a double bond at the terminal, $R^{b1}$, $R^{b3}$ and $R^{b4}$ have the same meanings as defined above, and "n1'" represents an integer selected from 0 to 10.

At this time, "n1'" in the above-mentioned formula (4) represents preferably an integer selected from 1 to 10.

By manufacturing the intermediate as mentioned above, occurrence of an internally rearranged product of the olefin can be suppressed in the manufacture of the symmetric hyperbranched silicone-modified polymerizable compound.

Also, it is preferred to use transition metal catalyst and radical scavenger in the hydrosilylation reaction.

By manufacturing the intermediate as mentioned above, occurrence of the internally rearranged product of the olefin can be more suppressed.

Moreover, the transition metal catalyst is preferably platinum catalyst.

Thus, in the modularized manufacturing method of the present invention, platinum catalyst can be used as the transition metal catalyst.

Further, it is preferred to use a compound represented by the following formula (5) or a compound represented by the following formula (6) as the compound having an unsaturated polymerizable functional group, and react it by using the intermediate represented by the above-mentioned formula (2) and catalyst.

$$R^{D'} \tag{5}$$

wherein $R^{D'}$ represents an unsaturated polymerizable compound having a reactive functional group.

$$R^{C'}R^D \tag{6}$$

wherein $R^D$ has the same meaning as defined above, and $R^{C'}$ represents a monovalent reactive group.

When such a modularized manufacturing method is employed, a symmetric hyperbranched silicone-modified polymerizable compound can be manufactured without impairing reactivity of the polymerizable functional group.

Moreover, it is preferred that the monovalent reactive group represented by $R^{C'}$ in the above-mentioned formula (6) is any of the reactive group selected from monovalent reactive groups represented by $X=R^YR^ZO$—, $T-X-R^Y_yR^ZO$—, $X=R^YCR^{Z'}R^{Z''}O$—, $T-X-R^Y_yCR^{Z'}R^{Z''}O$—, and oligoalkyleneoxy group having a reactive group at one terminal thereof, and having 2 to 10 carbon atoms and a repeating unit with an integer of 1 to 10;
wherein X, $R^Y$, $R^Z$, y, $R^{Z'}$ and $R^{Z''}$ have the same meanings as defined above, $R^{Y'}$ represents a trivalent functional group containing 0 or 1 of any atom selected from nitrogen atom, oxygen atom, sulfur atom, and carbon atom, and T represents a hydroxyl group, or any atom selected from chlorine atom and bromine atom.

When such a modularized manufacturing method is employed, it is possible to manufacture a symmetric hyperbranched silicone-modified polymerizable compound having higher flexibility.

At this time, $R^{D'}$ of the above-mentioned formula (5) is preferably an unsaturated polymerizable compound obtained by bonding an unsaturated group with a reactive functional group directly or through a linking group in the molecule, wherein the unsaturated group selected from acrylic group, methacrylic group, alkynyl group, styryl group, indenyl group, alkenyl group, cycloalkenyl group, norbornyl group, conjugated or non-conjugated alkadiene group and vinyl ether group each of which may contain a linear, branched or cyclic substituent having 1 to 10 carbon atoms and contain hetero atom(s), and the reactive functional group selected from hydroxyl group, amino group, hydroxycarbonyl group, aldehyde group, acid halide group, ester group, haloformate group, halogenated alkyl group, isocyanate group, isothiocyanate group, ketene group, phosphate group, epoxy group, aziridine group, tosyl group, mesyl group, trifluoromethanesulfonyl group, bromane group, iodane group, halogenated aryl group and nitroaryl group.

At this time, $R^D$ in the above-mentioned formula (6) is preferably a monovalent unsaturated polymerizable functional group selected from acrylic group, methacrylic group, alkynyl group, styryl group, indenyl group, alkenyl group, cycloalkenyl group, norbornyl group, conjugated or non-conjugated alkadiene group and vinyl ether group each of which may contain a linear, branched or cyclic substituent having 1 to 10 carbon atoms and contain hetero atom(s).

By using the compound having an unsaturated polymerizable functional group, it is possible to easily manufacture a symmetric hyperbranched silicone-modified polymerizable compound without impairing reactivity of the polymerizable functional group.

Moreover, in the above-mentioned modularized manufacturing method, it is preferred to use, as catalyst which is/are to be used when the intermediate represented by the above-mentioned formula (2) and the compound having an unsaturated polymerizable functional group are reacted, Lewis acid selected from one or more of organic or inorganic tin complex, titanium complex, iron complex, copper complex, zinc complex, aluminum complex, zirconium complex, yttrium complex, scandium complex, indium complex, lanthanum complex, cerium complex, samarium complex, europium complex and silicon complex or tertiary organic base, and to use the catalyst in an amount of 0.001 to 0.500 mol % based on the amount of the intermediate represented by the above-mentioned formula (2).

The modularized manufacturing method of the present invention can use such catalyst.

When the symmetric hyperbranched silicone-modified polymerizable compound of the present invention is employed, it is possible to obtain a material having flexibility, having good reactivity of the polymerizable functional group and having a branched structure which is positionally and sterically symmetric and pure than the conventional ones by introducing a glycerin structure having an ether group which is chemically high flexibility into the branched chain. Further, when the modularized manufacturing method of the present invention is employed, it is possible to manufacture a symmetric hyperbranched silicone-modified polymerizable compound by further suppressing occurrence of an internally rearranged product of olefin.

DETAILED DESCRIPTION OF THE PREFERRED EMBODIMENTS

The present inventor has intensively studied to solve the above-mentioned problems, and as a result, he has found out that a symmetric hyperbranched silicone-modified polymerizable compound having a branched structure which is positionally and sterically symmetric and pure than the conventional ones can be obtained by introducing a glycerin structure containing an ether group into the branched structure to possess flexibility to the branched structure and to improve reactivity of the polymerizable group, whereby accomplished the present invention.

The present invention provides a symmetric hyperbranched silicone-modified polymerizable compound (hereinafter sometimes abbreviated to as HB silicone) containing a compound represented by the following formula (1):

$$(R^A R^B)_2 CHOR^C_c R^D \qquad (1)$$

wherein $R^A$ represents a monovalent linear, branched or cyclic siloxane chain; $R^B$ represents $-CH_2CR^{b1}R^{b2}(CR^{b3}R^{b4})_{n1}OCH_2-$; wherein $R^{b1}$, $R^{b2}$, $R^{b3}$ and $R^{b4}$ each may be the same or different, and each represent a hydrogen atom or a divalent hydrocarbonylene methylene ether group which is a linear, branched or cyclic hydrocarbon group having 1 to 10 carbon atoms, each of which may be bonded, "n1" represents an integer selected from 0 to 10; $R^C$ represents a divalent linking group; "c" represents 0 or 1; and $R^D$ represents an unsaturated polymerizable functional group.

When such a HB silicone is employed, it is possible to obtain a material having a glycerin structure itself which has an ether group which is chemically high flexibility at the branched chain, having good reactivity of the polymerizable functional group and having a branched structure which is positionally and sterically symmetric and pure than the conventional ones.

The above-mentioned HB silicone is preferably a material in which n1 in the divalent hydrocarbonylene methylene ether group represented by $R^B$ in the above-mentioned formula (1) is an integer selected from 1 to 10, when "n1" represents 1, then $R^{b1}$ is a hydrocarbon group having 1 to 10 carbon atoms and $R^{b2}$ is a hydrogen atom to improve reactivity of the polymerizable functional group or to possess a branched structure which is positionally and sterically symmetric and purer.

When such a divalent hydrocarbonylene methylene ether group is introduced, occurrence of the internally rearranged product of the olefin which becomes the problem at the time of the manufacture mentioned later can be suppressed, and a HB silicone with purer and high purity can be obtained.

Moreover, to obtain a material having more flexibility, the divalent linking group represented by $R^C$ in the above-mentioned formula (1) is preferably any of the linking group selected from divalent linking groups represented by $-XR^Y_y R^Z O-$, $-XR^Y_y CR^{Z'} R^{Z''} O-$, and oligoalkyleneoxy group having 2 to 10 carbon atoms and a repeating unit with an integer of 1 to 10;

wherein X represents any one selected from $-CH_2-$, $-C(=O)-$, and $-C(=S)-$; $R^Y$ represents a divalent functional group containing 0 or 1 atom selected from nitrogen atom, oxygen atom, sulfur atom and carbon atom; $R^Z$ represents a linear, branched or cyclic alkylene group having 2 to 10 carbon atoms which may be substituted by an oxygen atom; "y" represents an integer selected from 0 or 1; and $R^{Z'}$ and $R^{Z''}$ each represent an alkyl group having 1 to 10 carbon atoms.

The method for manufacturing the HB silicone of the present invention may be exemplified by the following manufacturing method. By using glycerol-α,α'-diallyl ether (hereinafter sometimes abbreviated to as GDAE) which is a diallyl ether available from Tokyo Chemical Industry Co., Ltd., as a raw material, it was reacted with Karenz MOI [OCN$(CH_2)_2OC(=O)C(CH_3)=CH_2$] which is an isocyanate having a polymerizable group available from Showa Denko K.K. in the presence of organic iron complex catalyst, to obtain carbamic acid ester [$(CH_2=CHCH_2OCH_2)_2CHOC(=O)NH(CH_2)_2OC(=O)C(CH_3)=CH_2$] having a branch of diallyl with yield of 90%. To 1 molar equivalent of the above-mentioned carbamic acid ester was added 2 molar equivalent (1 molar equivalent of H-siloxane based on 1 molar equivalent of the allyl group) of a linear or branched H-siloxane and subjected to hydrosilylation reaction with platinum catalyst and toluene as solvent under the conditions of a reaction temperature of 70° C. According to this procedure, the HB silicone was obtained.

However, when a signal at the allyl group side is disappeared by the $^1$H-NMR, there is a case where the reaction excessively proceeds to a methacrylic group side which is not desired to perform the hydrosilylation reaction. As a result of the analysis by the $^1$H-NMR, the portion at which 1H is to be obtained with a hydrogen ratio of a methacrylic group was reduced to 0.6H. This result shows that 10 to 20% or so of an internally rearranged product at the olefin portion is formed at the allyl group, and an inner olefin which is the internally rearranged product does not react with the H-siloxane, so that the remained H-siloxane is also reacted with the methacrylic group. This problem can be solved by controlling an amount of the H-siloxane to be added since the reactivity of the methacrylic group is lower than that of the terminal olefin, but precise control of adding the H-siloxane is required and the operation is complicated which leads to increase in the manufacturing costs. Thus, as a method for surely retaining methacrylic group, it has been considered a method to retain the methacrylic portion by means of forming carbamic acid ester after subjecting to hydrosilylation reaction. However, even by the carbamic acid esterification after hydrosilylation reaction, only a product containing about 10% of an internally rearranged product of the olefin could be eventually obtained. The present inventor has further earnestly studied to solve the above-mentioned problems, and as a result, he has accomplished the modularized manufacturing method of the HB silicone of the present invention.

That is, the HB silicone of the present invention is preferably manufactured by the modularized manufacturing method which is to manufacture the compound represented by the above-mentioned formula (1) by reacting an intermediate represented by the following formula (2) and the compound having an unsaturated polymerizable functional group:

$$(R^A R^B)_2 CHOH \quad (2)$$

wherein $R^A$ and $R^B$ have the same meanings as defined above.

Here, the term modularized represents to manufacture a product by combining building blocks by a free combination where there are some building blocks that constitute the basic constitutional element. If the manufacturing method is employed, improvement to comply with the uses can be done by selecting suitable building blocks, and it is possible to commercialize the product quickly.

In the following, the best mode is explained with regard to the modularized manufacturing method of the present invention.

The compound represented by the above-mentioned formula (1) is preferably manufactured by the two-step method.

I) Step of Manufacturing the Intermediate Represented by the Above-Mentioned Formula (2)

The intermediate represented by the above-mentioned formula (2) is preferably manufactured by subjecting a compound represented by the following formula (3) and a compound represented by the following formula (4) to hydrosilylation reaction.

$$R^{A'} \quad (3)$$

wherein $R^{A'}$ represents a linear, branched or cyclic siloxane having one reactive hydrogen in the molecule, $$R^{B'}_2 CHOH \quad (4),$$

wherein $R^{B'}$ represents a monovalent hydrocarbonylene methylene ether group represented by $CH_2=CR^{b1}(CR^{b3}R^{b4})_{n1}OCH_2$- which has a double bond at the terminal, $R^{b1}$, $R^{b3}$ and $R^{b4}$ have the same meanings as defined above, and "n1'" represents an integer selected from 0 to 10.

Here, as $R^{A'}$ in the above-mentioned formula (3) which is one of the raw materials, it is not particularly limited so long as it is a siloxane having one reactive hydrogen in the molecule, and may be any of the structures of a linear, branched or cyclic.

Further, $R^{B'}$ in the above-mentioned formula (4) which is one of the raw materials is a monovalent hydrocarbonylene methylene ether group represented by $CH_2=CR^{b1}(CR^{b3}R^{b4})_{n1}OCH_2$— which has a double bond at the terminal, and "n1" among these is 0 to 10, preferably 1 to 10, and further preferably an integer selected from 1 to 5 in the point of easily obtained. If it is an integer selected from 1 to 10, it is more preferred since internal rearrangement of the olefin can be more effectively suppressed. Moreover, when it is a group wherein $R^{b1}$ is a methyl group or a hydrogen atom, $R^{b3}$ and $R^{b4}$ are hydrogen atoms and "n1'" represents an integer of 1 or 2, it is particularly preferred since occurrence of an internally rearranged product of the olefin can be more effectively suppressed.

Further, CHOH in the above-mentioned formula (4) is 2-substituted methanol, that is, it is preferably a material having a glycerin structure manufactured by the method in which a linear, branched or cyclic H-siloxane is subjected to hydrosilylation reaction by using glycerol-α,α'-di-3-butenyl ether (hereinafter sometimes abbreviated to as GDBE), glycerol-α,α'-di-4-pentenyl ether (hereinafter sometimes abbreviated to as GDPE), glycerol-α,α'-di-5-hexenyl ether (hereinafter sometimes abbreviated to as GDHE), glycerol-α,α'-di-6-heptenyl ether (hereinafter sometimes abbreviated to as GDHpE), glycerol-α,α'-dimethallyl ether (hereinafter sometimes abbreviated to as GDME), and glycerol-α,α'-diisoprenyl(3-methyl-3-butenyl) ether (hereinafter sometimes abbreviated to as GDiPE), in the presence of catalyst without solvent or in solvent. Moreover, in the above hydrosilylation reaction, 2,6-di(t-butyl)-1-hydroxytoluene (BHT) may be added as radical scavenger, which has an effect of suppressing the reaction of the H-siloxane and a hydroxyl group.

Here, in the above-mentioned manufacturing method of the di-substituted methanol, alcohol having an unsaturated bond may be used as the raw material. More specifically, 3-buten-1-ol (trade name: 3B1OL) or 4-penten-1-ol (trade name: 4P1OL) available from Hokko Chemical Industry Co., Ltd., 5-hexen-1-ol, 6-hepten-1-ol or β-methallyl alcohol available from Tokyo Chemical Industry Co., Ltd., and isoprenol (3-methyl-3-buten-1-ol) available from Merck & Co., may be used and those other than the above chain lengths, they can be obtained by synthesizing optionally. For example, ethyl-4-methyl-4-pentenoate available from Sigma-Aldrich Japan Co., LLC., is reduced by using lithium aluminum hydride (LiAlH$_4$) to obtain 4-methyl-4-penten-1-ol simply and easily. Also, a cyclic compound or a compound having a side chain longer than 2 carbon atoms may be obtained simply and easily, for example, by oxidizing 1,4-dihydroxycyclohexane commercially available from Tokyo Chemical Industry Co., Ltd., etc., by a general method such as PCC and Swern oxidation, etc., and subjecting to Wittig reaction with triphenylmethylphosphonium bromide and base to obtain 4-methylenecyclohexan-1-ol. There may be mentioned a method in which the alcohol having an unsaturated bond selected from these is mixed with epichlorohydrin available from Tokyo Chemical Industry Co., Ltd., potassium hydroxide available from Merck & Co., and tetrabutylammonium bromide available from Tokyo Chemical Industry Co., Ltd., as catalyst, and applying a synthetic method similar to that described in Nemoto, Hattori, et. al., Chemistry Letters, 2010, 39 (8), pp. 856-857, wherein the mixture is stirred at 45° C., neutralized with hydro-chloric acid, washed with water and a volatile component is removed by distillation.

In the above-mentioned hydrosilylation reaction, the H-siloxane is preferably used with a suitable amount, 0.90 to 1.00 molar equivalent of the H-siloxane is more preferably used based on one terminal alkenyl group of the compound represented by the above-mentioned formula (4), and further preferably 0.95 to 1.00 molar equivalent of the H-siloxane is used based on one terminal alkenyl group. In the present invention, since occurrence of the internally rearranged product of the olefin in the hydrosilylation reaction can be suppressed, adjustment of an amount of the H-siloxane to be used, in particular, reduction thereof becomes easy, and sufficient effects can be shown even with an amount of the H-siloxane mentioned above.

Further, in the above hydrosilylation reaction, the catalyst may be used alone or may be used by diluting with solvent, etc., more preferably transition metal catalyst, further preferably selected from platinum catalysts of chloroplatinic acid hexahydrate [Speier catalyst], Karstedt catalyst ($Pt_2[[(CH_2=CH)(CH_3)_2Si]_2O]_3$), Ashby catalyst ($Pt_4[CH_2=CHSi(CH_3)O]_4$) and Lamoreaux catalyst (platinum-octanal/octanol complex), and the most preferred catalyst is Karstedt catalyst or Ashby catalyst.

In the above-mentioned hydrosilylation reaction, it may be without solvent or solvent may be used, and when the solvent is used, it is preferably selected from a substituted or unsubstituted aromatic hydrocarbon compound having 6 to 12 carbon atoms including a hydrocarbon group selected from 1 to 6 carbon atoms; a substituted or unsubstituted saturated alicyclic hydrocarbon compound having 5 to 12 carbon atoms containing a linear, branched or cyclic hydrocarbon group selected from 1 to 6 carbon atoms; a linear, branched or cyclic amide compound in which a linear, branched or cyclic hydrocarbon compound having 1 to 8 carbon atoms may be substituted on the nitrogen; a linear, branched or cyclic ether compound containing 1 to 3 oxygen atoms in which a linear, branched or cyclic saturated or unsaturated hydrocarbon compound having 1 to 8 carbon atoms may be substituted independently on an oxygen atom; a linear, branched or cyclic ketone compound having 1 to 7 carbon atoms which may be substituted by oxygen atom; a linear, branched or cyclic alkylnitrile having 1 to 6 carbon atoms; a linear, branched or cyclic and saturated or unsaturated halogenated hydrocarbon compound having 1 to 10 carbon atoms; and alcohol compound which is a linear or branched hydrocarbon compound selected from 1 to 6 carbon atoms.

Such solvent may be selected from, for example, toluene, o-xylene, m-xylene, p-xylene, 1,3,5-mesitylene, 1,2,3-mesitylene, 1,2,4-mesitylene, ethylbenzene, n-propylbenzene, i-propylbenzene, n-butylbenzene, i-butylbenzene, sec-butylbenzene, t-butylbenzene, n-pentylbenzene, i-pentylbenzene, sec-pentylbenzene, t-pentylbenzene, n-hexylbenzene, i-hexylbenzene, sec-hexylbenzene, t-hexylbenzene, cyclopentane, cyclohexane, cycloheptane, cyclooctane, methylcyclohexane, ethylcyclohexane, propylcyclohexane, n-butylcyclohexane, i-butylcyclohexane, sec-butylcyclohexane, t-butylcyclohexane, n-pentylcyclohexane, i-pentylcyclohexane, sec-pentylcyclohexane, t-pentylcyclohexane, n-hexylcyclohexane, i-hexylcyclohexane, sec-hexylcyclohexane, t-hexylcyclohexane, limonene, N,N'-dimethylformamide (DMF), N,N'-dimethylformacetamide (DMAc), 1,3-dimethyl-2-imidazolidinone (DMI), 1,3-dimethyl-3,4,5,6-tetrahydro-2(1H)-pyrimidinone (DMPU), diethyl ether, t-butyl methyl ether (TBME), dibutyl ether, cyclopentylmethyl ether (CPME), diphenyl ether, dimethoxymethane (DMM), 1,2-dimethoxyethane, diethylene glycol dimethyl ether, tetrahydrofuran (THF), tetrahydropyran (THP), dioxane, 2-methyltetrahydrofuran, 2-ethyltetrahydrofuran, acetone, methyl ethyl ketone (MEK), methyl isobutyl ketone (MIBK), cyclopentanone, cyclohexanone, cycloheptanone, acetonitrile, propionitrile, butyronitrile, α,α,α-trifluoromethylbenzene, chlorobenzene, chloroform, dichloromethane, 1,2-dichloroethane, methanol, ethanol, 1-propanol, 2-propanol (IPA), n-butyl alcohol, i-butyl alcohol, sec-butyl alcohol, t-butyl alcohol, 1,2-ethylene glycol, 1,3-propylene glycol, 1,2-dihydroxypropane, 2-methoxyethanol and 2-(2-methoxyethoxy) ethanol, and more preferably without solvent or toluene, ethylbenzene, methylcyclohexane, ethylcyclohexane, ethanol or IPA.

Incidentally, the intermediate represented by the above-mentioned formula (2) obtained by the above-mentioned procedures may substitute the hydrogen atom in $R^{B'}$ with a hydrocarbon group by the substitution reaction when $R^{b2}$ in $R^B$ possessed by the HB silicone (the above-mentioned formula (1)) to be manufactured is made a hydrocarbon group having 1 to 10 carbon atoms. By subjecting to such a reaction, flexibility of the HB silicone can be adjusted.

II) A Step of Reacting the Intermediate Represented by the Above-Mentioned Formula (2) and the Compound Having an Unsaturated Polymerizable Functional Group It is preferred by using a compound represented by the following formula (5) or a compound represented by the following formula (6) as the compound having an unsaturated polymerizable functional group, the reaction is carried out by using the intermediate represented by the above-mentioned formula (2) and catalyst.

wherein $R^{D'}$ represents an unsaturated polymerizable compound having a reactive functional group.

wherein $R^D$ has the same meaning as defined above, and $R^{C'}$ represents a monovalent reactive group.

Further, the unsaturated polymerizable compound having a reactive group of $R^{D'}$ of the above-mentioned formula (5) is preferably an unsaturated polymerizable compound obtained by directly bonding an unsaturated group selected from any of acrylic group, methacrylic group, alkynyl group, styryl group, indenyl group, alkenyl group, cycloalkenyl group, norbornyl group, conjugated or non-conjugated alkadiene group and vinyl ether group each of which may have a linear, branched or cyclic substituent(s) having 1 to 10 carbon atoms and contain hetero atom, with a reactive functional group selected from any of hydroxyl group, amino group, hydroxycarbonyl group, aldehyde group, acid halide group (acid chloride group, acid bromide group, acid iodide group, etc.), ester group, haloformate group (chloroformate group, bromoformate group, etc.), halogenated alkyl group (chloroalkyl group, bromoalkyl group, iodoalkyl group, etc.), isocyanate group, isothiocyanate group, ketene group, phosphate group, epoxy group, aziridine group, tosyl group, mesyl group, trifluoromethanesulfonyl group, bromane group, iodane group, halogenated aryl group (chloroaryl group, bromoaryl group, iodoaryl group, etc.) and nitroaryl group, and may be used by optionally synthesizing or may be used a commercially available product. The commercially available product may be mentioned methacrylic acid, methacrylic acid chloride, glycidyl methacrylate, acrylic acid, acrylic acid chloride, chloromethylstyrene, 4-vinylbenzoic acid, 2-chlorostyrene, 3-chlorostyrene, 4-chlorostyrene, 2-bromostyrene, 3-bromostyrene, 4-bromostyrene, 2-chloromethylstyrene, 3-chloromethylstyrene, 4-chloromethylstyrene, 2-bromomethylstyrene, 3-bromomethylstyrene, 4-bromomethylstyrene, 1,3-butadiene, 1,3-pentadiene, 1,4-pentadiene, 1,3-hexadiene, 1,4-hexadiene, 1,5-hexadiene, 1,3-heptadiene, 1,4-heptadiene, 1,5-heptadiene, 1,6-heptadiene, 3-butyn-1-ol, 4-pentyn-1-ol, 5-hexyn-1-ol, 9-decyn-1-ol, 10-undecen-1-ol, propiolic acid and 5-hexynoic acid all of which are available from Tokyo Chemical Industry Co., Ltd., or 2-hydroxypropyl acrylate (trade name: HPA) and 4-hydroxybutyl acrylate (trade name: 4-HBA) all of which are available from Osaka Organic Chemical Industry Ltd., and among these, acrylic acid chloride and methacrylic acid chloride are particularly preferred.

$R^D$ in the above-mentioned formula (6) is preferably a monovalent unsaturated polymerizable functional group selected from any of acrylic group, methacrylic group, alkynyl group, styryl group, indenyl group, alkenyl group, cycloalkenyl group, norbornyl group, conjugated or non-conjugated alkadiene group and vinyl ether group, each of which may have a linear, branched or cyclic substituent(s) having 1 to 10 carbon atoms and contain hetero atom.

$R^{C'}$ in the above-mentioned formula (6) is a monovalent reactive group, and preferably any of a reactive group selected from monovalent reactive groups represented by $X=R^Y R^Z O-$, $T-X-R^Y_y R^Z O-$, $X=R^{Y'} CR^{Z'} R^{Z''} O-$, $T-X-R^Y_y CR^{Z'} R^{Z''} O-$, and oligoalkyleneoxy group having a reactive group at one terminal thereof, and having 2 to 10 carbon atoms and a repeating unit with an integer of 1 to 10;

wherein X, $R^Y$, $R^Z$, "y", $R^{Z'}$ and $R^{Z''}$ have the same meanings as defined above, $R^{Y'}$ represents a trivalent functional group containing 0 or 1 of any atom selected from nitrogen atom, oxygen atom, sulfur atom, and carbon atom, and T represents a hydroxyl group, or an atom selected from chlorine atom and bromine atom.

The compound ($R^{C'} R^D$) represented by the above-mentioned formula (6) may be mentioned an isocyanate group-containing radical polymerizable compound, an isothiocyanate group-containing radical polymerizable compound, a ketene group-containing radical polymerizable compound, a chloromethyl group-containing radical polymerizable compound and an oligoalkylene oxide group-containing radical polymerizable compound.

Among these, the isocyanate group-containing radical polymerizable compound may be used those optionally synthesized, or may be used a commercially available product. As the above-mentioned commercially available product, there may be mentioned, for example, a (meth)-acryl compound having an isocyanate such as Karenz MOI [OCN$(CH_2)_2 OC(=O)$ $C(CH_3)=CH_2$], Karenz MOI-EG [OCN$(CH_2)_2 O(CH_2)_2 OC(=O)$ $C(CH_3)=CH_2$] or Karenz AOI [OCN$(CH_2)_2 OC(=O)CH=CH_2$] all available from Showa Denko K.K., and 3-isopropenyl-α,α-dimethylbenzylisocyanate available from Tokyo Chemical Industry Co., Ltd., etc. Further, typical examples when the synthesized product is used may be mentioned an isocyanate group-containing radical polymerizable compound, which can be obtained by treating a carboxylic acid compound having a corresponding polymerizable group with i-butyl chloroformate or pivaloyl chloride, etc., to obtain a mixed acid anhydride, reacting with sodium azide to obtain an acid azide compound, and subjecting the obtained acid azide to Curtius rearrangement by heating under stirring, or reacting an alkylamine compound having a corresponding polymerizable group with triphosgene at 40° C. by heating under stirring.

The isothiocyanate group-containing radical polymerizable compound may be used those optionally synthesized, and for example, an isothiocyanate group-containing radical polymerizable compound can be obtained by chlorinating alkyl alcohol having a corresponding polymerizable group and 1 to 10 carbon atoms by oxalyl chloride or thionyl chloride, brominating the same with carbon tetrabromide or boron tribromide, iodating the same with N-iodosuccinimide or sodium iodide, tosylating the same with p-toluenesulfonic acid chloride and triethylamine or mesylating the same with methanesulfonic acid chloride and triethylamine to obtain a compound having an eliminatable group, and reacting the resulting compound with potassium thiocyanate.

The ketene group-containing radical polymerizable compound may be used those optionally synthesized, which is $CH_2=C(CH_3)C(=O)O-R^1-C=C=O$ wherein $R^1$ is a linear, branched or cyclic alkylene group having 1 to 6 carbon atoms in which an oxygen atom may be contained therein, specifically mentioned 3-(1-oxoprop-1-enyl) methacrylate, 4-(1-oxobut-1-enyl) methacrylate, 5-(1-oxopent-1-enyl) methacrylate, 6-(1-oxohex-1-enyl) methacrylate, 7-(1-oxohept-1-enyl) methacrylate, 8-(1-oxooct-1-enyl) methacrylate, 6-(2-ethyl-1-oxohex-1-enyl) methacrylate and 2-(3-oxoprop-2-ene-1-oxy)ethyl methacrylate. The synthetic method thereof is explained by referring to $CH_2=C(CH_3)C(=O)OCH_2CH=C=O$ as a representative example. A commercially available $CH_2=C(CH_3)C(=O)O(CH_2)_3 OH$ is oxidized by chromic acid or Jones reagent, etc., the resulting carboxylic acid $CH_2=C(CH_3)$ $C(=O)$ $O(CH_2)_2 C(=O)$OH is chlorinated by chlorinating agent such as thionyl chloride, oxalyl chloride, triphosgene, phosgene, phosphoryl chloride, etc., to prepare acid chloride $CH_2=C(CH_3)C(=O)O(CH_2)_2 C(=O)Cl$, and treating the same with tertiary organic base having a medium degree basicity such as triethylamine, etc.

The chloromethyl group-containing radical polymerizable compound may be used those optionally synthesized, and as a synthesis method, for example, it can be synthesized by reacting methacrylic acid and anhydrous sodium carbonate to form potassium methacrylate, and by adding bromochloromethane as such to simply and easily synthesize chloromethyl methacrylate. Or else, 2-hydroxyethyl methacrylate (HEMA) and sodium hydride are reacted to form sodium salt, and bromochloromethane is added thereto as such to simply and easily synthesize 2-(chloromethoxy)ethyl methacrylate. Thus, when the polymerizable group has a hydroxy group, synthesis can be carried out simply and easily.

The oligoalkylene oxide-containing radical polymerizable compound may be used those optionally synthesized, or may be used a commercially available product. The commercially available product may be mentioned 2-hydroxyethyl methacrylate, ethylene glycol monoacetoacetate monomethacrylate, ethylene glycol monovinyl ether and diethylene glycol monovinyl ether all available from Tokyo Chemical Industry Co., Ltd. Also, an oligoalkylene oxide-containing radical polymerizable compound having a reactive functional group can be obtained by 4-nitrophenylcarbonating a material having a hydroxyl group at one terminal end thereof by 4-nitrophenyl chloroformate, and the material may be mentioned a poly- or oligoalkylene oxide where one terminal end of which is methacrylic group as a polymerizable group and the other terminal end of which is a hydroxyl group such as BLEMMER PE-90, BLEMMER PE-200, BLEMMER PE-350, BLEMMER PP-1000, BLEMMER PP-800, BLEMMER PP-500, BLEMMER 50PEP-300, BLEMMER 70PEP-350B, BLEMMER 55PEP-800 and BLEMMER 10PEP-500B all available from NOF Corporation, and a poly- or oligoalkylene oxide where one terminal end of which is an acrylic group as a polymerizable group and the other terminal end of which is a hydroxyl group such as BLEMMER AE-90, BLEMMER AE-200, BLEMMER AE-400, BLEMMER AP-150, BLEMMER AP-400, BLEMMER AP-550, BLEMMER AP-800, etc., all available from NOF Corporation.

Among the compounds exemplified above, the compound ($R^{C'} R^D$) represented by the above-mentioned formula (6) is preferably a polymerizable group having a reactive functional group selected from isocyanate group-containing acrylate, isocyanate group-containing methacrylate, isocyanate group and ethylene glycol group-containing methacrylate, thioisocyanate group-containing acrylate, thioisocyanate group-containing methacrylate, ketene group-containing acrylate, ketene group-containing methacrylate, chloromethyl group-containing acrylate, chloromethyl group-containing methacrylate and oligoalkylene oxide-containing methacrylate, particularly preferably a polymerizable group having a reactive functional group selected from isocyanate group-containing acrylate, isocyanate group-containing methacrylate, isocyanate group and ethylene glycol group-containing methacrylate, and thioisocyanate group-containing acrylate.

Next, the catalyst to be used for reacting the above-mentioned intermediate represented by the above-mentioned formula (2) and the above-mentioned compound having an unsaturated polymerizable functional group is preferably Lewis acid selected from one or more of an organic or inorganic tin complex, titanium complex, iron complex, copper complex, zinc complex, aluminum complex, zirconium complex, yttrium complex, scandium complex, indium complex, lanthanum complex, cerium complex, samarium complex, europium complex and silicon complex, or tertiary organic base, and preferably used in an amount of 0.001 to 0.500 mol % based on the amount of the intermediate represented by the above-mentioned formula (2).

The inorganic or organic tin compound may be mentioned dibutyltin dilaurate, dibutyltin maleate, dibutyltin phthalate, dibutyltin dioctanoate, dibutyltin bis(2-ethylhexanoate), dibutyltin bis(methyl maleate), dibutyltin bis(ethyl maleate), dibutyltin bis(butyl maleate), dibutyltin bis(octyl maleate), dibutyltin bis(tridecyl maleate), dibutyltin bis(benzyl maleate), dibutyltin diacetate, dibutyltin bisisooctylthioglycolate, dibutyltin bis-2-ethylhexylthioglycolate, dioctyltin bis(ethylmaleate), dioctyltin bis(octyl maleate), dibutyltin dimethoxide, dibutyltin bis(nonyl phenoxide), dibutenyltin oxide, dibutyltin oxide, dibutyltin bis(acetylacetonate), dibutyltin bis(ethylacetylacetonate), reaction product of dibutyltin oxide and silicate compound, reaction product of dibutyltin oxide and phthalic acid ester, etc.

The inorganic or organic titanium complex catalyst may be mentioned, for example, tetrabutyl titanate, tetrapropyl titanate, tetraisopropyl titanate, titanium tetrakis(acetylacetonate), titanium diisopropoxybis(acetylacetonate), titanium diisopropoxybis(ethyl acetate), or complex in which diol such as tartaric acid is reacted with titanium chloride, etc.

The inorganic or organic iron complex catalyst may be mentioned iron chloride, iron bromide, iron acetylacetonate, iron triflate, iron acetate, iron pyridine complex, iron bipyridyl complex, iron terpyridyl complex, iron pincer complex, iron imine complex, iron salen complex, iron tetramethylenediamine complex, iron ethylenediamine complex, iron ephedrine complex, iron carbonyl complex, iron dienyl complex, ferrocene complex, etc.

The inorganic or organic copper complex catalyst may be mentioned copper chloride, copper bromide, copper acetylacetonate, copper triflate, copper acetate, copper pyridine complex, copper bipyridyl complex, copper pincer complex, copper imine complex, copper salen complex, copper tetramethylenediamine complex, copper ethylenediamine complex, copper ephedrine complex, copper carbonyl complex, copper dienyl complex, etc.

The inorganic or organic zinc complex catalyst may be mentioned zinc chloride, zinc bromide, zinc chloride, zinc bromide, zinc acetylacetonate, zinc triflate, zinc acetate, zinc pyridine complex, zinc bipyridyl complex, zinc terpyridyl complex, zinc pincer complex, zinc imine complex, zinc salen complex, zinc tetramethylenediamine complex, zinc ethylenediamine complex, zinc ephedrine complex, zinc carbonyl complex, zinc dienyl complex, etc.

The inorganic or organic aluminum complex catalyst may be mentioned aluminum chloride, aluminum bromide, aluminum acetylacetonate, aluminum triflate, aluminum acetate, aluminum pyridine complex, aluminum bipyridyl complex, aluminum pincer complex, aluminum imine complex, aluminum salen complex, aluminum tetramethylenediamine complex, aluminum ethylenediamine complex, aluminum ephedrine complex, methyl aluminoxane (common name: MAO) prepared by adding water to trimethylaluminum, etc.

The inorganic or organic zirconium complex catalyst may be mentioned zirconium chloride, zirconium bromide, zirconium acetylacetonate, zirconium triflate, zirconium acetate, zirconium pyridine complex, zirconium bipyridyl complex, zirconium terpyridyl complex, zirconium pincer complex, zirconium imine complex, zirconium salen complex, zirconium tetramethylenediamine complex, zirconium ethylenediamine complex, zirconium ephedrine complex, zirconium carbonyl complex, zirconium dienyl complex, zirconocene chloride, etc.

The inorganic or organic yttrium complex catalyst may be mentioned yttrium chloride, yttrium bromide, yttrium acetylacetonate, yttrium triflate, yttrium acetate, yttrium pyridine complex, yttrium bipyridyl complex, yttrium terpyridyl complex, yttrium pincer complex, yttrium imine complex, yttrium salen complex, yttrium tetramethylenediamine complex, yttrium ethylenediamine complex, yttrium ephedrine complex, yttrium carbonyl complex, yttrium dienyl complex, etc.

The inorganic or organic scandium complex catalyst may be mentioned scandium chloride, scandium bromide, scandium acetylacetonate, scandium carbonate, scandium triflate, scandium acetate, scandium pyridine complex, scandium bipyridyl complex, scandium terpyridyl complex, scandium pincer complex, scandium imine complex, scandium salen complex, scandium tetramethylenediamine complex, scandium ethylenediamine complex, scandium ephedrine complex, scandium carbonyl complex, scandium dienyl complex, etc.

The inorganic or organic indium complex catalyst may be mentioned indium chloride, indium bromide, indium acetylacetonate, indium triflate, indium acetate, indium pyridine complex, indium bipyridyl complex, indium pincer complex, indium imine complex, indium salen complex, indium tetramethylenediamine complex, indium ethylenediamine complex, indium ephedrine complex, indium carbonyl complex, etc.

The inorganic or organic lanthanum complex catalyst may be mentioned lanthanum chloride, lanthanum bromide, lanthanum acetylacetonate, lanthanum triflate, lanthanum acetate, lanthanum pyridine complex, lanthanum bipyridyl complex, lanthanum terpyridyl complex, lanthanum pincer complex, lanthanum imine complex, lanthanum salen complex, lanthanum tetramethylenediamine complex, lanthanum ethylenediamine complex, lanthanum ephedrine complex, lanthanum carbonyl complex, lanthanum dienyl complex, etc.

The inorganic or organic cerium complex catalyst may be mentioned cerium chloride, cerium bromide, cerium carbonate, cerium acetylacetonate, cerium triflate, cerium acetate, cerium pyridine complex, cerium bipyridyl complex, cerium terpyridyl complex, cerium pincer complex, cerium imine complex, cerium salen complex, cerium tetramethylenediamine complex, cerium ethylenediamine complex, cerium ephedrine complex, cerium carbonyl complex, cerium dienyl complex, etc.

The inorganic or organic samarium complex catalyst may be mentioned samarium chloride, samarium bromide, samarium iodide cerium carbonate, samarium acetylacetonate, samarium triflate, samarium acetate, samarium pyridine complex, samarium bipyridyl complex, samarium terpyridyl complex, samarium pincer complex, samarium imine complex, samarium salen complex, samarium tetramethylenediamine complex, samarium ethylenediamine complex, samarium ephedrine complex, samarium carbonyl complex, samarium dienyl complex, etc.

The inorganic or organic europium complex catalyst may be mentioned europium chloride, europium bromide, europium iodide cerium carbonate, europium acetylacetonate, europium triflate, europium acetate, europium pyridine complex, europium bipyridyl complex, europium terpyridyl complex, europium pincer complex, europium imine complex, europium salen complex, europium tetramethylenediamine complex, europium ethylenediamine complex, europium ephedrine complex, europium carbonyl complex, europium dienyl complex, etc.

The inorganic or organic silicon complex catalyst may be mentioned silicon chloride, silicon bromide, silicon carbonate, silicon acetylacetonate, silicon triflate, silicon acetate, silicon pyridine complex, silicon bipyridyl complex, silicon terpyridyl complex, silicon pincer complex, silicon imine complex, silicon salen complex, silicon tetramethylenediamine complex, silicon ethylenediamine complex, silicon ephedrine complex, silicon carbonyl complex, silicon dienyl complex, etc. The silicon complex may be mentioned trimethylsilyl triflate.

Also, the tertiary organic base may be mentioned trimethylamine, triethylamine ($Et_3N$), diisopropylethylamine (DIPEA), tri-n-butylamine, tri-n-pentylamine, tri-n-hexylamine, tri-n-heptylamine, tri-n-octylamine, N-methylpyrrolidine, N-methylpiperidine, N-methylmorpholine (NMO), N,N,N', N'-tetramethylethylenediamine (TMEDA), N-methylimidazole (NMI), pyridine, 2,6-lutidine, 1,3,5-collidine, N,N-dimethylamino pyridine (DMAP), pyrazine, quinoline, 1,8-diazabicyclo-[5,4,0]-7-undecene (DBU), 1,4-diazabicyclo-[2,2,2]octane (DABCO), etc. In this reaction, more preferred materials are tetraisopropyl titanate, dibutyltin dilaurate, iron acetylacetonate and $Et_3N$, and among these, the most preferred is iron acetylacetonate.

The above-mentioned catalyst preferably used is organic iron complex in the points of toxicity and reactivity, and an amount of the catalyst preferably used is 0.001 to 0.500 mol % based on the amount of the intermediate represented by the above-mentioned formula (2), more preferably 0.005 to 0.050 mol %. If it is 0.001 mol % or more, the reaction easily proceeds, while if it is 0.500 mol % or less, the reaction system is not colored so that it is preferred. The most preferred range is 0.005 to 0.01 mol % in view of toxicity and reactivity.

In the above-mentioned reaction, it may be without solvent or solvent may be used, and when the solvent is used, it is preferably selected from a substituted or unsubstituted aromatic hydrocarbon compound having 6 to 12 carbon atoms including a hydrocarbon group selected from 1 to 6 carbon atoms; a substituted or unsubstituted saturated alicyclic hydrocarbon compound having 5 to 12 carbon atoms containing a linear, branched or cyclic hydrocarbon group selected from 1 to 6 carbon atoms; a linear, branched or cyclic amide compound in which a linear, branched or cyclic hydrocarbon compound having 1 to 8 carbon atoms may be substituted on the nitrogen; a linear, branched or cyclic ether compound containing 1 to 3 oxygen atoms in which a linear, branched or cyclic saturated or unsaturated hydrocarbon compound having 1 to 8 carbon atoms may be substituted independently on an oxygen atom; a linear, branched or cyclic alkylnitrile having 1 to 6 carbon atoms; and a linear, branched or cyclic and saturated or unsaturated halogenated hydrocarbon compound having 1 to 10 carbon atoms.

In the above-mentioned reaction, it may be without solvent or solvent may be used, and when the solvent is used, aprotic solvent may be used alone or in admixture. Such solvent may be selected from, for example, toluene, o-xylene, m-xylene, p-xylene, 1,3,5-mesitylene, 1,2,3-mesitylene, 1,2,4-mesitylene, ethylbenzene, n-propylbenzene, i-propylbenzene, n-butylbenzene, butylbenzene, sec-butylbenzene, t-butylbenzene, n-pentylbenzene, i-pentylbenzene, sec-pentylbenzene, t-pentylbenzene, n-hexylbenzene, i-hexylbenzene, sec-hexylbenzene, t-hexylbenzene, cyclopentane, cyclohexane, cycloheptane, cyclooctane, methylcyclohexane, ethylcyclohexane, propylcyclohexane, n-butylcyclohexane, i-butylcyclohexane, sec-butylcyclohexane, t-butylcyclohexane, n-pentylcyclohexane, i-pentylcyclohexane, sec-pentylcyclohexane, t-pentylcyclohexane, n-hexylcyclohexane, i-hexylcyclohexane, sec-hexylcyclohexane, t-hexylcyclohexane, limonene, N,N'-dimethylformamide (DMF), N,N'-dimethylformacetamide (DMAc), 1,3-dimethyl-2-imidazolidinone (DMI), 1,3-dimethyl-3,4,5,6-tetrahydro-2(1H)-pyrimidinone (DMPU), diethyl ether, t-butylmethyl ether (TBME), dibutyl ether, cyclopentylmethyl ether (CPME), diphenyl ether, tetrahydrofuran (THF), dimethoxymethane (DMM), 1,2-dimethoxyethane, diethylene glycol dimethyl ether, tetrahydropyran (THP), 1,4-dioxane, 2-methyltetrahydrofuran, 2-ethyltetrahydrofuran, acetone, methylethyl ketone (MEK), methyl isobutyl ketone (MIBK), cyclopentanone, cyclohexanone, cycloheptanone, acetonitrile, propionitrile, butyronitrile, α,α,α-trifluoromethylbenzene, chlorobenzene, chloroform, dichloromethane and 1,2-dichloroethane, more preferred are toluene, ethylbenzene, methylcyclohexane and ethylcyclohexane, and the most preferred is toluene or without solvent.

The HB silicone thus obtained can be made a single polymer or a silicone-modified composition containing a copolymer with the other polymerizable compound. The other polymerizable compound is not particularly limited, and a suitable material may be used depending on the uses mentioned later.

Such a silicone-modified composition can be suitably used for paint, ophthalmic device composition, or cosmetic composition. Further, such cosmetic composition may be exemplified by a material for skin care, hair, antiperspirant, deodorant, makeup, or ultraviolet protective.

EXAMPLES

In the following, the present invention is explained by referring to Synthetic Examples and Examples, but the present invention is not limited by the following examples, and it is possible to carry out the embodiment by suitably modifying the same, any of which are included in the technical scope of the present invention.

Incidentally, in this Example, a measurement of the molecular structure was mainly carried out by nuclear magnetic resonance spectrometry ($^1$H-NMR, $^{13}$C-NMR) and infrared spectroscopy (IR), and a molecular weight distribution was performed by gel permeation chromatography (in the following, it is sometimes abbreviated to as GPC) measurement was carried out with tetrahydrofuran (THF) solution.

Synthetic Example 1

Synthesis of GDBE [$CH_2=CH(CH_2)_2 OCH_2]_2CHOH$

Into a three-necked flask equipped with a thermometer, a stirring device and a dropping funnel attached to a nitrogen-introducing tube were charged 3-buten-1-ol (3.5 mol), potassium hydroxide (3.2 mol) and tetrabutylammonium bromide (0.2 mol), after the mixture was stirred at room temperature, epichlorohydrin (1.0 mol) was added to the dropping funnel, and added dropwise to the mixture so that an inner temperature was maintained to 45° C. After dropwise addition, the mixture was stirred at 60° C. by using an oil bath, and after confirming that a signal (2 to 3 ppm) of $^1$H-NMR derived from glycidyl ether has disappeared, the reaction temperature was returned to room temperature, neutralized by 4M hydrochloric acid, washed with water, treated by a saturated saline solution, treated by sodium sulfate and filtered, then, the alcohol as a raw material was removed by distillation under reduced pressure, and the residue was evaporated (130° C./600 Pa) to obtain the product. The spectroscopic data were as follows:

$^1$H-NMR (400 MHz, CDCl$_3$) δ 2.34 (tq, J=1.2, 6.7 Hz, 4H), 3.48 (dd, J=9.8, 6.3 Hz, 4H), 3.53 (dd, J=6.8, 1.6 Hz, 4H), 3.94 (ddd, J=11.6, 6.2, 3.8 Hz, 1H), 5.04 (dq, J=9.1, 1.6 Hz, 2H), 5.09 (dq, J=17.2, 1.7 Hz, 2H), 5.81 (ddd, J=17.2, 9.1, 6.7 Hz, 2H).

$^{13}$C-NMR (100 MHz, CDCl$_3$) δ 34.14 (CH$_2$×2), 69.50 (CH), 70.82 (CH$_2$×2), 71.94 (CH$_2$×2), 116.56 (CH$_2$=CH× 2), 135.16 (CH$_2$=CH×2).

IR (NaCl) ν 914, 995, 1023, 1112, 1382, 2864, 3077, 3442.

[CH$_2$=CH(CH$_2$)$_2$OCH$_2$]$_2$CHOH could be synthesized with a yield of 82%.

Synthetic Example 2

Synthesis of GDME [CH$_2$=C(CH$_3$)CH$_2$OCH$_2$]$_2$CHOH

Synthesis was carried out in the same manner as in Synthetic Example 1 except for changing 3-buten-1-ol therein to β-methallyl alcohol. Incidentally, the conditions of the distillation (130° C./600 Pa) are the same as in those of [Synthetic Example 1] to obtain the product. The spectroscopic data were as follows:

$^1$H-NMR (400 MHz, CDCl$_3$) δ 2.34 (tq, J=1.2, 6.7 Hz, 4H), 3.48 (dd, J=9.8, 6.3 Hz, 4H), 3.53 (dd, J=6.8, 1.6 Hz, 4H), 3.94 (ddd, J=11.6, 6.2, 3.8 Hz, 1H), 5.04 (dq, J=9.1, 1.6 Hz, 2H), 5.09 (dq, J=17.2, 1.7 Hz, 2H), 5.81 (ddd, J=17.2, 9.1, 6.7 Hz, 2H).

$^{13}$C-NMR (100 MHz, CDCl$_3$) δ 34.14 (CH$_2$×2), 69.50 (CH), 70.82 (CH$_2$×2), 71.94 (CH$_2$×2), 116.56 (CH$_2$=CH× 2), 135.16 (CH$_2$=CH×2).

IR (NaCl) ν 914, 995, 1023, 1112, 1382, 2864, 3077, 3442.

[CH$_2$=C(CH$_3$)CH$_2$OCH$_2$]$_2$CHOH could be synthesized with a yield of 80%.

Synthetic Example 3

Synthesis of GDiPE [CH$_2$=C(CH$_3$)(CH$_2$)$_2$OCH$_2$]$_2$CHOH

Synthesis was carried out in the same manner as in Synthetic Example 1 except for changing 3-buten-1-ol therein to 3-methyl-3-buten-1-ol. Incidentally, the product was obtained with the conditions of the distillation (135° C./250 Pa). The spectroscopic data were as follows:

$^1$H-NMR (400 MHz, CDCl$_3$) δ 2.34 (tq, J=1.2, 6.7 Hz, 4H), 3.48 (dd, J=9.8, 6.3 Hz, 4H), 3.53 (dd, J=6.8, 1.6 Hz, 4H), 3.94 (ddd, J=11.6, 6.2, 3.8 Hz, 1H), 5.04 (dq, J=9.1, 1.6 Hz, 2H), 5.09 (dq, J=17.2, 1.7 Hz, 2H), 5.81 (ddd, J=17.2, 9.1, 6.7 Hz, 2H).

$^{13}$C-NMR (100 MHz, CDCl$_3$) δ 34.14 (CH$_2$×2), 69.50 (CH), 70.82 (CH$_2$×2), 71.94 (CH$_2$×2), 116.56 (CH$_2$=CH× 2), 135.16 (CH$_2$=CH×2).

IR (NaCl) ν 914, 995, 1023, 1112, 1382, 2864, 3077, 3442.

[CH$_2$=C(CH$_3$) (CH$_2$)$_2$OCH$_2$]$_2$CHOH could be synthesized with a yield of 76%.

Synthetic Example 4

Synthesis of [[Bu[Si(CH$_3$)$_2$O]$_4$Si(CH$_3$)$_2$ (CH$_2$)$_4$OCH$_2$]$_2$CHOH Into a 100 mL three-necked flask equipped with a thermometer, a magnetic stirrer bar and a nitrogen-introducing tube were charged 20.6 g (49.9 mmol) of 1-butyl-9-hydro-1,1,3,3,5,5,7,7,9,9-decamethylpentasiloxane (H-siloxane), 11.1 g (30 wt %) of toluene and 3.7 mg (100 ppm) of BHT, a dropping funnel in which 5.00 g (25.0 mmol) of GDBE of Synthetic Example 1 had been charged was mounted to the flask, and an inner temperature was raised to 70° C. under stirring. To the mixture was added a 0.5 wt % toluene solution of 21.9 mg (3 ppm) of Karstedt catalyst (Karstedt, Pt$_2$ [[(CH$_2$=CH)(CH$_3$)$_2$Si]$_2$O]$_3$) by a microsyringe, the resulting mixture was stirred at the same temperature for 10 minutes, and GDBE was continuously added dropwise so that an inner temperature does not exceed 75° C. After exotherm was ceased, $^1$H-NMR was measured, and it was confirmed that a signal of the terminal olefin has disappeared. Thereafter, the reaction temperature was returned to room temperature, and the residual H-siloxane and toluene were removed by distillation under reduced pressure (130° C./<1 KPa), to obtain a colorless transparent oily product. The spectroscopic data of the obtained product were a molecular weight distribution Mw/Mn=1.01 and as follows:

$^1$H-NMR (400 MHz, CDCl$_3$) δ 0.04 (s, 36H), 0.06 (s, 24H), 0.49-0.59 (m, 8H), 0.88 (t, J=6.9 Hz, 6H), 3.49-3.52 (m, 8H), 3.90-3.97 (m, 1H).

$^{13}$C-NMR (75 MHz, CDCl$_3$) δ 0.09 (CH$_3$×8), 0.77 (CH$_3$× 4), 0.87 (CH$_3$×8), 13.51 (CH$_2$×2), 17.73 (CH$_2$×2), 17.82 (CH$_2$×2), 19.60 (CH$_2$×2), 25.24 (CH$_2$×2), 26.08 (CH$_2$×2), 32.98 (CH$_2$×2), 69.22 (CH), 71.01 (CH$_2$×2), 71.89 (CH$_2$×2).

IR (NaCl) ν 796, 1031, 1259, 2873, 2925, 3473.

[[Bu[Si(CH$_3$)$_2$O]$_4$Si(CH$_3$)$_2$ (CH$_2$)$_4$OCH$_2$]$_2$CHOH could be synthesized with a yield of 94%.

Synthetic Example 5

Synthesis of [[(CH$_3$)$_3$SiO]$_2$Si(CH$_3$)(CH$_2$)$_4$OCH$_2$]$_2$CHOH

According to the same molar ratio and operation procedure as in Synthetic Example 4 except for changing 1-butyl-9-hydro-1,1,3,3,5,5,7,7,9,9-decamethylpentasiloxane thereof to 3-hydro-1,1,1,3,5,5,5-heptamethyltrisiloxane, a colorless transparent oily product was obtained. The spectroscopic data of the obtained product were as follows:

$^1$H-NMR (400 MHz, CDCl$_3$) δ 0.00 (s, 6H), 0.05-0.12 (m, 36H), 0.46 (t, J=8.4 Hz, 4H), 1.31-1.43 (m, 4H), 1.60 (quin., J=6.9 Hz, 4H), 3.41-3.52 (m, 8H), 3.89-3.97 (m, 1H).

$^{13}$C-NMR (75 MHz, CDCl$_3$) δ−0.51 (CH$_3$×2), 1.62 (CH$_3$× 4), 17.18 (CH$_2$×2), 19.49 (CH$_2$×2), 32.80 (CH$_2$×2), 69.26 (CH), 71.04 (CH$_2$×2), 71.92 (CH$_2$×2).

IR (NaCl) ν 756, 795, 1032, 1172, 1256, 2957, 3443.

[[(CH$_3$)$_3$SiO]$_2$Si(CH$_3$)(CH$_2$)$_4$OCH$_2$]$_2$CHOH could be synthesized with a yield of 85%.

Synthetic Example 6

Synthesis of [[Bu[Si(CH$_3$)$_2$O]$_4$Si(CH$_3$)$_2$]CH$_2$CH(CH$_3$)CH$_2$OCH$_2$]$_2$CHOH According to the same molar ratio and operation procedure as in Synthetic Example 4 except for changing GDBE thereof to GDME obtained in Synthetic Example 2, a colorless transparent oily product was obtained. The spectroscopic data of the obtained product were as follows:

$^1$H-NMR (400 MHz, CDCl$_3$) δ 0.00 (s, 6H), 0.05-0.12 (m, 36H), 0.46 (t, J=8.4 Hz, 4H), 1.31-1.43 (m, 4H), 1.60 (quin., J=6.9 Hz, 4H), 3.41-3.52 (m, 8H), 3.89-3.97 (m, 1H).

$^{13}$C-NMR (75 MHz, CDCl$_3$) δ−0.51 (CH$_3$×2), 1.62 (CH$_3$× 4), 17.18 (CH$_2$×2), 19.49 (CH$_2$×2), 32.80 (CH$_2$×2), 69.26 (CH), 71.04 (CH$_2$×2), 71.92 (CH$_2$×2).

IR (NaCl) ν 756, 795, 1032, 1172, 1256, 2957, 3443.

[[Bu[Si(CH$_3$)$_2$O]$_4$Si(CH$_3$)$_2$]CH$_2$CH(CH$_3$)CH$_2$OCH$_2$]$_2$CHOH could be synthesized with a yield of 90%.

Synthetic Example 7

Synthesis of [[Bu[Si(CH$_3$)$_2$O]$_4$Si(CH$_3$)$_2$]CH$_2$CH(CH$_3$)(CH$_2$)$_2$OCH$_2$]$_2$CHOH According to the same molar ratio and operation procedure as in Synthetic Example 4 except for changing GDBE thereof to GDiPE obtained in Synthetic Example 3, a colorless transparent oily product was obtained. The spectroscopic data of the obtained product were as follows:

$^1$H-NMR (400 MHz, CDCl$_3$) δ 0.00 (s, 6H), 0.05-0.12 (m, 36H), 0.46 (t, J=8.4 Hz, 4H), 1.31-1.43 (m, 4H), 1.60 (quin., J=6.9 Hz, 4H), 3.41-3.52 (m, 8H), 3.89-3.97 (m, 1H).

$^{13}$C-NMR (75 MHz, CDCl$_3$) δ−0.51 (CH$_3$×2), 1.62 (CH$_3$× 4), 17.18 (CH$_2$×2), 19.49 (CH$_2$×2), 32.80 (CH$_2$×2), 69.26 (CH), 71.04 (CH$_2$×2), 71.92 (CH$_2$×2).

IR (NaCl) ν 756, 795, 1032, 1172, 1256, 2957, 3443.

[[Bu[Si(CH$_3$)$_2$O]$_4$Si(CH$_3$)$_2$]CH$_2$CH(CH$_3$)(CH$_2$)$_2$OCH$_2$]$_2$CHOH could be synthesized with a yield of 90%.

Synthetic Example 8

Synthesis of [[(CH$_3$)$_3$SiC]$_2$Si(CH$_3$)CH$_2$CH(CH$_3$)(CH$_2$)$_2$OCH$_2$]$_2$CHOH According to the same molar ratio and operation procedure as in Synthetic Example 5 except for changing GDBE thereof to GDiPE obtained in Synthetic Example 3, a colorless transparent oily product was obtained. The spectroscopic data of the obtained product were as follows:

$^1$H-NMR (400 MHz, CDCl$_3$) δ 0.00 (s, 6H), 0.05-0.12 (m, 36H), 0.46 (t, J=8.4 Hz, 4H), 1.31-1.43 (m, 4H), 1.60 (quin., J=6.9 Hz, 4H), 3.41-3.52 (m, 8H), 3.89-3.97 (m, 1H).

$^{13}$C-NMR (75 MHz, CDCl$_3$) δ−0.51 (CH$_3$×2), 1.62 (CH$_3$× 4), 17.18 (CH$_2$×2), 19.49 (CH$_2$×2), 32.80 (CH$_2$×2), 69.26 (CH), 71.04 (CH$_2$×2), 71.92 (CH$_2$×2).

IR (NaCl) ν 756, 795, 1032, 1172, 1256, 2957, 3443.

[[(CH$_3$)$_3$SiO]$_2$Si(CH$_3$)CH$_2$CH(CH$_3$)(CH$_2$)$_2$OCH$_2$]$_2$CHOH could be obtained with a yield of 86%.

Synthetic Example 9

Synthesis of [Bu[Si(CH$_3$)$_2$O]$_4$Si(CH$_3$)$_2$(CH$_2$)$_3$OCH$_2$]$_2$CHOH

According to the same molar ratio and operation procedure as in Synthetic Example 1 except for changing GDBE of Synthetic Example 4 to GDAE ([CH$_2$=CHCH$_2$OCH$_2$]$_2$CHOH), a colorless transparent oily product was obtained. The spectroscopic data of the obtained product were a molecular weight distribution Mw/Mn=1.01 and as follows:

$^1$H-NMR (400 MHz, CDCl$_3$) δ 0.00-0.14 (m, 60H), 0.44-0.69 (m, 8H), 0.88 (t, J=6.6 Hz, 6H), 1.23-1.39 (m, 8H), 1.45-1.66 (m, 8H), 3.37-3.78 (m, 9H).

$^{13}$C-NMR (75 MHz, CDCl$_3$) δ 0.04 (CH$_3$×8), 0.72 (CH$_3$× 4), 0.82 (CH$_3$×8), 13.39 (CH$_2$×2), 17.70 (CH$_2$×2), 17.77 (CH$_2$×2), 19.53 (CH$_2$×2), 25.19 (CH$_2$×2), 33.00 (CH$_2$×2), 69.15 (CH), 70.99 (CH$_2$×2), 71.88 (CH$_2$×2).

IR (NaCl) ν 797, 841, 1032, 1161, 1259, 2875, 2930, 3433.

[Bu[Si(CH$_3$)$_2$O]$_4$Si(CH$_3$)$_2$(CH$_2$)$_3$OCH$_2$]$_2$CHOH could be obtained with a yield of 93%.

Synthetic Example 10

Synthesis of [(CH$_3$)$_3$SiO]$_2$Si(CH$_3$)(CH$_2$)$_3$OCH$_2$]$_2$CHOH

According to the same molar ratio and operation procedure as in Synthetic Example 9 except for changing 1-butyl-9-hydro-1,1,3,3,5,5,7,7,9,9-decamethylpentasiloxane thereof to 3-hydro-1,1,1,3,5,5,5-heptamethyltrisiloxane, a colorless transparent oily product was obtained. The spectroscopic data of the obtained product were a molecular weight distribution Mw/Mn=1.01 and as follows:

$^1$H-NMR (400 MHz, CDCl$_3$) δ 0.01 (s, 6H), 0.09 (s, 36H), 0.45 (t, J=8.4 Hz, 4H), 1.60 (quin., J=7.8 Hz, 4H), 2.47 (dd, J=4.0, 1.2 Hz, 1H), 3.37-3.53 (m, 8H), 3.95 (q, J=5.4 Hz, 1H).

$^{13}$C-NMR (75 MHz, CDCl$_3$) δ−0.63 (CH$_3$×2), 1.50 (CH$_3$× 12), 13.31 (CH$_2$×2), 17.89 (CH$_3$), 63.40 (CH), 69.23 (CH$_2$× 2), 71.09 (CH$_2$).

IR (NaCl) ν 755, 782, 769, 841, 1049, 1258, 2957, 3454.

[(CH$_3$)$_3$SiO]$_2$Si(CH$_3$)(CH$_2$)$_3$OCH$_2$]$_2$CHOH could be obtained with a yield of 89%.

Example 1

Synthesis of [[Bu[Si(CH$_3$)$_2$O]$_4$Si(CH$_3$)$_2$(CH$_2$)$_4$OCH$_2$]$_2$CHOC(=O)NH(CH$_2$)$_2$OC(=O) C(CH$_3$)=CH$_2$ In a 100 mL three-necked flask equipped with a thermometer, a dropping funnel and a nitrogen-introducing tube, and placed a magnetic stirrer bar, 20.5 g (20.0 mol) of the above-mentioned [[Bu[Si(CH$_3$)$_2$O]$_4$Si(CH$_3$)$_2$(CH$_2$)$_4$OCH$_2$]$_2$CHOH obtained in Synthetic Example 4 was charged therein, and 0.35 mg (50 μmol %) of iron acetyl acetate[Fe(acac)$_3$] catalyst available from Dojindo Laboratories and 2.40 mg (100 ppm) of BHT were added thereto, and the mixture was heated to 40° C. under stirring. To the mixture was added dropwise from a dropping funnel 3.26 g (21.0 mol) of Karenz MOI so as to not exceed an inner temperature of 45° C. The resulting mixture was stirred for 30 minutes at the same temperature, and when a signal (5.00 ppm) derived from the carbamic acid ester was formed with an amount of 1H by $^1$H-NMR, the reaction temperature was returned to room temperature, 71 mg (0.3 wt %) of activated charcoal was added to the mixture and the resulting mixture was stirred at room temperature for one hour. Thereafter, the activated charcoal was filtered off, and a slightly excessive amount of Karenz MOI was removed by distillation under reduced pressure (90 to 100° C./<1KPa) to obtain a pale yellow transparent oily product. The spectroscopic data of the obtained product were a molecular weight distribution Mw/Mn=1.01 and as follows:

$^1$H-NMR (400 MHz, CDCl$_3$) δ 0.06-0.10 (m, 60H), 0.49-0.58 (m, 8H), 0.88 (t, J=6.9 Hz, 6H), 1.24-1.43 (m, 12H), 1.59 (quin., J=1.0 Hz, 3H), 3.47-3.62 (m, 10H), 4.22 (t, J=5.2 Hz, 20H), 6.11 (dd, J=1.3, 0.8 Hz, 1H), 5.59 (quin., J=1.5 Hz, 1H), 4.95-5.07 (m, 2H), 5.59 (quin., J=1.5 Hz, 1H), 6.11 (dd, J=1.3, 0.8 Hz, 1H).

$^{13}$C-NMR (75 MHz, CDCl$_3$) δ 0.06 (CH$_3$×8), 0.63 (CH$_3$×4), 0.80 (CH$_3$×8), 13.37 (CH$_2$×2), 17.82 (CH$_2$×2), 17.83 (CH$_2$×2), 19.55 (CH$_2$×2), 25.30 (CH$_2$×2), 25.99 (CH$_2$×2), 33.02 (CH$_2$×2), 40.65 (CH$_2$), 63.21 (CH$_2$), 68.77 (CH), 71.11 (CH$_2$×2), 71.84 (CH$_2$×2), 125.25 (CH$_2$=C(CH$_3$)), 136.01 (CH$_2$=C(CH$_3$)), 155.69 (C=O), 166.66 (C=O).

IR (NaCl) ν 798, 840, 1033, 1160, 1259, 1725, 2926, 2959, 3356.

[[Bu[Si(CH$_3$)$_2$O]$_4$Si(CH$_3$)$_2$ (CH$_2$)$_4$OCH$_2$]$_2$CHOC(=O)NH(CH$_2$)$_2$OC(=O)C(CH$_3$)=CH$_2$ could be obtained with a yield of 78%.

Example 2

Synthesis of [[(CH$_3$)$_3$SiO]$_2$Si(CH$_3$) (CH$_2$)$_4$OCH$_2$]$_2$CHOC(=O)NH(CH$_2$)$_2$OC(=O)C(CH$_3$)=CH$_2$ According to the same molar ratio and operation procedure as in Example 1 except for changing [[Bu[Si(CH$_3$)$_2$O]$_4$Si(CH$_3$)$_2$ (CH$_2$)$_4$OCH$_2$]$_2$CHOH of Example 1 to [[(CH$_3$)$_3$SiO]$_2$Si(CH$_3$) (CH$_2$)$_4$OCH$_2$]$_2$CHOH obtained in Synthetic Example 5, a pale yellow transparent oily product was obtained. The spectroscopic data of the obtained product were a molecular weight distribution Mw/Mn=1.01 and as follows:

$^1$H-NMR (400 MHz, CDCl$_3$) δ−0.01 (s, 6H), 0.04-0.13 (m, 36H), 0.37-0.50 (m, 4H), 1.46-1.66 (m, 4H), 1.94 (t, J=1.3 Hz, 3H), 3.33-3.54 (m, 6H), 3.54-3.65 (m, 4H), 4.22 (t, J=5.2 Hz, 2H), 4.96-5.07 (m, 2H), 5.59 (t, J=1.6 Hz, 1H), 6.11 (s, 1H).

$^{13}$C-NMR (75 MHz, CDCl$_3$) δ−0.66 (CH$_3$×2), 1.52 (CH$_3$×12), 13.29 (CH$_2$×2), 17.91 (CH$_3$), 23.0 (CH$_2$×2), 39.91 (CH$_2$), 63.36 (CH$_2$), 69.11 (CH$_2$×2), 71.75 (CH$_2$), 73.73 (CH$_2$×2), 125.30 (CH$_2$=C(CH$_3$)), 135.88 (CH$_2$=C), 155.73 (O=O), 166.62 (C=O).

IR (NaCl) ν 755, 797, 1049, 1162, 1258, 1725, 2958, 3356.

[[(CH$_3$)$_3$SiO]$_2$Si(CH$_3$) (CH$_2$)$_4$OCH$_2$]$_2$CHOC(=O)NH(CH$_2$)$_2$OC(=O) (CH$_3$)=CH$_2$ could be obtained with a yield of 73%.

Example 3

Synthesis of [[(CH$_3$)$_3$SiO]$_2$Si(CH$_3$) (CH$_2$)$_4$OCH$_2$]$_2$CHOC(=O)NH [(CH$_2$)$_2$O]$_2$C(=O)C(CH$_3$)=CH$_2$ According to the same molar ratio and operation procedure as in Example 1 except for changing Karenz MOI to Karenz MOI-EG by using the disiloxane [[Bu[Si(CH$_3$)$_2$O]$_4$Si(CH$_3$)$_2$ (CH$_2$)$_4$OCH$_2$]$_2$CHOH obtained in Synthetic Example 4, a pale yellow transparent oily product was obtained. The spectroscopic data of the obtained product were as follows:

$^1$H-NMR (400 MHz, CDCl$_3$) δ 0.00-0.18 (m, 60H), 0.45-0.58 (m, 8H), 0.88 (t, J=6.9 Hz, 6H), 1.23-1.38 (m, 8H), 1.48-1.63 (m, 8H), 1.95 (s, 3H), 3.30-3.48 (m, 4H), 3.50-3.64 (m, 8H), 3.69 (t, J=4.6 Hz, 2H), 4.28 (t, J=4.6 Hz, 2H), 4.93-5.02 (m, 1H), 5.07-5.18 (m, 1H), 5.58 (s, 1H), 6.13 (s, 1H).

$^{13}$C-NMR (75 MHz, CDCl$_3$) δ−0.14 (CH$_3$×4), −0.08 (CH$_3$×4), 0.78 (CH$_3$×4), 0.87 (CH$_3$×8), 13.49 (CH$_2$×2), 13.96 (CH$_2$×2), 17.97 (CH$_3$), 23.22 (CH$_2$×2), 25.23 (CH$_2$×2), 26.06 (CH$_2$×2), 40.66 (CH$_2$), 63.35 (CH$_2$), 68.75 (CH), 69.82 (CH$_2$), 71.92 (CH$_2$), 73.93 (CH$_2$×2), 125.22 (CH$_2$=C(CH$_3$)), 135.99 (CH$_2$=C(CH$_3$)), 155.74 (C=O), 166.70 (C=O).

IR (NaCl) ν 779, 839, 1034, 1167, 1259, 1725, 2927, 2959, 3356.

[[(CH$_3$)$_3$SiO]$_2$Si(CH$_3$) (CH$_2$)$_4$OCH$_2$]$_2$CHOC(=O)NH [(CH$_2$)$_2$O]$_2$C(=O) C(CH$_3$)=CH$_2$ could be obtained with a yield of 83%.

Example 4

Synthesis of [[Bu[Si(CH$_3$)$_2$O]$_4$Si(CH$_3$)$_2$]CH$_2$CH(CH$_3$)CH$_2$OCH$_2$]$_2$CHOC(=O)NH(CH$_2$)$_2$OC(=O)C(CH$_3$)=CH$_2$ According to the same molar ratio and operation procedure as in Example 1 except for changing [[Bu[Si(CH$_3$)$_2$O]$_4$Si(CH$_3$)$_2$ (CH$_2$)$_4$OCH$_2$]$_2$CHOH of Example 1 to [[Bu[Si(CH$_3$)$_2$O]$_4$Si(CH$_3$)$_2$]CH$_2$CH(CH$_3$)CH$_2$OCH$_2$]$_2$CHOH obtained in Synthetic Example 6, a pale yellow transparent oily product was obtained. The spectroscopic data of the obtained product were a molecular weight distribution Mw/Mn=1.01 and as follows:

$^1$H-NMR (400 MHz, CDCl$_3$) δ−0.01 (s, 6H), 0.04-0.13 (m, 36H), 0.37-0.50 (m, 4H), 1.46-1.66 (m, 4H), 1.94 (t, J=1.3 Hz, 3H), 3.33-3.54 (m, 6H), 3.54-3.65 (m, 4H), 4.22 (t, J=5.2 Hz, 2H), 4.96-5.07 (m, 2H), 5.59 (t, J=1.6 Hz, 1H), 6.11 (s, 1H).

$^{13}$C-NMR (75 MHz, CDCl$_3$) δ−0.66 (CH$_3$×2), 1.52 (CH$_3$×12), 13.29 (CH$_2$×2), 17.91 (CH$_3$), 23.0 (CH$_2$×2), 39.91 (CH$_2$), 63.36 (CH$_2$), 69.11 (CH$_2$×2), 71.75 (CH$_2$), 73.73 (CH$_2$×2), 125.30 (CH$_2$=C(CH$_3$)), 135.88 (CH$_2$=C), 155.73 (C=O), 166.62 (C=O).

IR (NaCl) ν 755, 797, 1049, 1162, 1258, 1725, 2958, 3356.

[[Bu[Si(CH$_3$)$_2$O]$_4$Si(CH$_3$)$_2$]CH$_2$CH(CH$_3$)CH$_2$OCH$_2$]$_2$CHOC(=O)NH(CH$_2$)$_2$OC(=O)C(CH$_3$)=CH$_2$ could be obtained with a yield of 72%.

Example 5

Synthesis of [[Bu[Si(CH$_3$)$_2$O]$_4$Si(CH$_3$)$_2$]CH$_2$CH(CH$_3$) (CH$_2$)$_2$OCH$_2$]$_2$CHOC(=O)NH(CH$_2$)$_2$OC(=O)C(CH$_3$)=CH$_2$ According to the same molar ratio and operation procedure as in Example 1 except for changing [[Bu[Si(CH$_3$)$_2$O]$_4$Si(CH$_3$)$_2$]CH$_2$CH(CH$_3$) (CH$_2$)$_2$OCH$_2$]$_2$CHOH obtained in Synthetic Example 7, a pale yellow transparent oily product was obtained. The spectroscopic data of the obtained product were a molecular weight distribution Mw/Mn=1.01 and as follows:

$^1$H-NMR (400 MHz, CDCl$_3$) δ−0.01 (s, 6H), 0.04-0.13 (m, 36H), 0.37-0.50 (m, 4H), 1.46-1.66 (m, 4H), 1.94 (t, J=1.3 Hz, 3H), 3.33-3.54 (m, 6H), 3.54-3.65 (m, 4H), 4.22 (t, J=5.2 Hz, 2H), 4.96-5.07 (m, 2H), 5.59 (t, J=1.6 Hz, 1H), 6.11 (s, 1H).

$^{13}$C-NMR (75 MHz, CDCl$_3$) δ−0.66 (CH$_3$×2), 1.52 (CH$_3$×12), 13.29 (CH$_2$×2), 17.91 (CH$_3$), 23.0 (CH$_2$×2), 39.91 (CH$_2$), 63.36 (CH$_2$), 69.11 (CH$_2$×2), 71.75 (CH$_2$), 73.73

(CH$_2$×2), 125.30 (CH$_2$=C(CH$_3$)), 135.88 (CH$_2$=C), 155.73 (0=0), 166.62 (C=O).

IR (NaCl) ν 755, 797, 1049, 1162, 1258, 1725, 2958, 3356.

[[Bu[Si(CH$_3$)$_2$O]$_4$Si(CH$_3$)$_2$]CH$_2$CH(CH$_3$) (CH$_2$)$_2$OCH$_2$]$_2$CHOC(=O) N H(CH$_2$)$_2$OC(=O)C(CH$_3$)=CH$_2$ could be obtained with a yield of 72%.

Example 6

Synthesis of [[(CH$_3$)$_3$SiO]$_2$Si(CH$_3$)CH$_2$CH(CH$_3$) (CH$_2$)$_2$OCH$_2$]$_2$CHOC(=O)NH(CH$_2$)$_2$OC(=O)C(CH$_3$)=CH$_2$ According to the same molar ratio and operation procedure as in Example 1 except for changing [[Bu[Si(CH$_3$)$_2$O]$_4$Si(CH$_3$)$_2$ (CH$_2$)$_4$OCH$_2$]$_2$CHOH of Example 1 to [[(CH$_3$)$_3$SiO]$_2$Si(CH$_3$)CH$_2$CH(CH$_3$)(CH$_2$)$_2$OCH$_2$]$_2$CHOH obtained in Synthetic Example 8, a pale yellow transparent oily product was obtained. The spectroscopic data of the obtained product were a molecular weight distribution Mw/Mn=1.01 and as follows:

$^1$H-NMR (400 MHz, CDCl$_3$) δ −0.01 (s, 6H), 0.04-0.13 (m, 36H), 0.37-0.50 (m, 4H), 1.46-1.66 (m, 4H), 1.94 (t, J=1.3 Hz, 3H), 3.33-3.54 (m, 6H), 3.54-3.65 (m, 4H), 4.22 (t, J=5.2 Hz, 2H), 4.96-5.07 (m, 2H), 5.59 (t, J=1.6 Hz, 1H), 6.11 (s, 1H).

$^{13}$C-NMR (75 MHz, CDCl$_3$) δ −0.66 (CH$_3$×2), 1.52 (CH$_3$×12), 13.29 (CH$_2$×2), 17.91 (CH$_3$), 23.0 (CH$_2$×2), 39.91 (CH$_2$), 63.36 (CH$_2$), 69.11 (CH$_2$×2), 71.75 (CH$_2$), 73.73 (CH$_2$×2), 125.30 (CH$_2$=C(CH$_3$)), 135.88 (CH$_2$=C), 155.73 (0=0), 166.62 (0=0).

IR (NaCl) ν 755, 797, 1049, 1162, 1258, 1725, 2958, 3356.

[[(CH$_3$)$_3$SiO]$_2$Si(CH$_3$)CH$_2$CH(CH$_3$) (CH$_2$)$_2$OCH$_2$]$_2$CHOC(=O)NH(CH$_2$)$_2$OC(=O)C(CH$_3$)=CH$_2$ could be obtained with a yield of 75%.

Example 7

Synthesis of [[Bu[Si(CH$_3$)$_2$O]$_4$Si(CH$_3$)$_2$]CH$_2$CH(CH$_3$) (CH$_2$)$_2$OCH$_2$]$_2$CHOC(=O)NH(CH$_2$)$_2$OC(=O) C(CH$_3$)=CH$_2$ According to the same molar ratio and operation procedure as in Example 1 except for changing [[Bu[Si(CH$_3$)$_2$O]$_4$Si(CH$_3$)$_2$(CH$_2$)$_4$OCH$_2$]$_2$CHOH and Karenz MOI of Example 1 to [[Bu[Si(CH$_3$)$_2$O]$_4$Si(CH$_3$)$_2$]CH$_2$CH(CH$_3$)(CH$_2$)$_2$OCH$_2$]$_2$CHOH obtained in Synthetic Example 7 and Karenz MOI-EG, a pale yellow transparent oily product was obtained. The spectroscopic data of the obtained product were a molecular weight distribution Mw/Mn=1.01 and as follows:

$^1$H-NMR (400 MHz, CDCl$_3$) δ −0.01 (s, 6H), 0.04-0.13 (m, 36H), 0.37-0.50 (m, 4H), 1.46-1.66 (m, 4H), 1.94 (t, J=1.3 Hz, 3H), 3.33-3.54 (m, 6H), 3.54-3.65 (m, 4H), 4.22 (t, J=5.2 Hz, 2H), 4.96-5.07 (m, 2H), 5.59 (t, J=1.6 Hz, 1H), 6.11 (s, 1H).

$^{13}$C-NMR (75 MHz, CDCl$_3$) δ −0.66 (CH$_3$×2), 1.52 (CH$_3$×12), 13.29 (CH$_2$×2), 17.91 (CH$_3$), 23.0 (CH$_2$×2), 39.91 (CH$_2$), 63.36 (CH$_2$), 69.11 (CH$_2$×2), 71.75 (CH$_2$), 73.73 (CH$_2$×2), 125.30 (CH$_2$=C(CH$_3$)), 135.88 (CH$_2$=C), 155.73 (0=0), 166.62 (C=O).

IR (NaCl) ν 755, 797, 1049, 1162, 1258, 1725, 2958, 3356.

[[Bu[Si(CH$_3$)$_2$O]$_4$Si(CH$_3$)$_2$]CH$_2$CH(CH$_3$) (CH$_2$)$_2$OCH$_2$]$_2$CHOC(=O) N H(CH$_2$)$_2$OC(=O) C(CH$_3$)=CH$_2$ could be obtained with a yield of 76%.

Example 8

Synthesis of [[Bu[Si(CH$_3$)$_2$O]$_4$Si(CH$_3$)$_2$ (CH$_2$)$_3$OCH$_2$]$_2$CHOC(=O)NH(CH$_2$)$_2$OC(=O)C(CH$_3$)=CH$_2$ According to the same molar ratio and operation procedure as in Example 1 except for changing [[Bu[Si(CH$_3$)$_2$O]$_4$Si(CH$_3$)$_2$ (CH$_2$)$_4$OCH$_2$]$_2$CHOH of Example 1 to [[Si(CH$_3$)$_2$O]$_4$Si(CH$_3$)$_2$ (CH$_2$)$_3$OCH$_2$]$_2$CHOH obtained in Synthetic Example 9, a pale yellow transparent oily product was obtained. The spectroscopic data of the obtained product were a molecular weight distribution Mw/Mn=1.01 and as follows:

$^1$H-NMR (400 MHz, CDCl$_3$) δ 0.00-0.12 (m, 60H), 0.46-0.56 (m, 8H), 0.88 (t, J=6.9 Hz, 6H), 1.25-1.35 (m, 8H), 1.50-1.65 (m, 8H), 1.94 (s, 3H), 3.42-3.65 (m, 10H), 4.22 (t, J=4.7 Hz, 2H), 4.88-5.06 (m, 2H), 5.59 (t, J=1.5 Hz, 1H), 6.11 (s, 1H).

$^{13}$C-NMR (75 MHz, CDCl$_3$) δ 0.08 (CH$_3$×8), 0.65 (CH$_3$×4), 0.83 (CH$_3$×8), 13.67 (CH$_2$×2), 17.84 (CH$_2$×2), 17.85 (CH$_2$×2), 19.56 (CH$_2$×2), 25.32 (CH$_2$×2), 33.04 (CH$_2$×2), 40.67 (CH$_2$), 63.23 (CH$_2$), 68.79 (CH), 71.13 (CH$_2$×2), 71.86 (CH$_2$×2), 125.28 (CH$_2$=C(CH$_3$)), 135.99 (CH$_2$=C(CH$_3$)), 155.70 (0=0), 166.68 (0=0).

IR (NaCl) ν 798, 839, 1033, 1162, 1259, 1725, 2873, 2926, 2959, 3356.

[[Bu[Si(CH$_3$)$_2$O]$_4$Si(CH$_3$)$_2$(CH$_2$)$_3$OCH$_2$]$_2$CHOC(=O)NH(CH$_2$)$_2$OC(=O)C(CH$_3$)=CH$_2$ could be obtained with a yield of 67%.

Example 9

Synthesis of [[Bu[Si(CH$_3$)$_2$O]$_4$Si(CH$_3$)$_2$ (CH$_2$)$_3$OCH$_2$]CHOC(=O)NH(CH$_2$)$_2$OC(=O)C(CH$_3$)=CH$_2$ According to the same molar ratio and operation procedure as in Example 2 except for changing [[Bu[Si(CH$_3$)$_2$O]$_4$Si(CH$_3$)$_2$ (CH$_2$)$_3$OCH$_2$]$_2$CHOH of Example 8 to [(CH$_3$)$_3$SiO]$_2$Si(CH$_3$)(CH$_2$)$_3$OCH$_2$]$_2$CHOH obtained in Synthetic Example 10, a pale yellow transparent oily product was obtained. The spectroscopic data of the obtained product were a molecular weight distribution Mw/Mn=1.01 and as follows:

$^1$H-NMR (400 MHz, CDCl$_3$) δ 0.00 (s, 6H), 0.03-0.15 (m, 36H), 0.38-0.49 (m, 4H), 1.95 (t, J=1.2 Hz, 3H), 3.32-3.55 (m, 6H), 3.56-3.67 (m, 4H), 4.23 (t, J=5.6 Hz, 2H), 4.93-5.08 (m, 2H), 5.60 (t, J=1.2 Hz, 1H), 6.11 (s, 1H).

$^{13}$C-NMR (75 MHz, CDCl$_3$) δ −0.63 (CH$_3$×2), 1.50 (CH$_3$×12), 13.31 (CH$_2$×2), 17.89 (CH$_3$), 39.93 (CH$_2$), 63.40 (CH$_2$), 69.15 (CH$_2$×2), 71.79 (CH$_2$), 73.75 (CH$_2$×2), 125.25 (CH$_2$=C(CH$_3$)), 135.86 (CH$_2$=C), 155.70 (0=0), 166.60 (0=0).

IR (NaCl) ν 756, 798, 1051, 1160, 1256, 1726, 2927, 2960, 3355.

[[Bu[Si(CH$_3$)$_2$O]$_4$Si(CH$_3$)$_2$ (CH$_2$)$_3$OCH$_2$]$_2$CHOC(=O)NH(CH$_2$)$_2$OC(=O)C(CH$_3$)=CH$_2$ could be obtained with a yield of 99%.

In $^1$H-NMR, $^{13}$C-NMR or IR of Examples 1 to 9, disilicone which is a main product was shown, and a formed amount of a monosilicone which is a by-product formed by internally rearranging the olefin was a little so that it could not be totally assigned by NMR or IR. Thus, an amount of the internally rearranged product of the olefin was measured by GPC measurement using THF solvent. When the amount of the internally rearranged product of Example 8 was made 100, the relative values of the respective Examples were shown in Table 1. In Examples 8 and 9, an allyl group was used as a group for reacting with the H-siloxane, the internally rearranged product of the olefin by the hydrosilylation reaction was present but the objective HB silicone could be obtained. Further, by using an isoprenyl group as a group for reacting with the H-siloxane as in Examples 5 to 7, it could be realized to make the internally rearranged product 0.

TABLE 1

|  | Example 1 | Example 2 | Example 3 | Example 4 | Example 5 | Example 6 | Example 7 | Example 8 | Example 9 |
|---|---|---|---|---|---|---|---|---|---|
| Internally rearranged product | 50 | 70 | 50 | 3 | 0 | 0 | 0 | 100 | 190 |

The HB silicone thus obtained is a material having flexibility by introducing glycerin having an ether group which has chemically high flexibility into the side chain, having good reactivity of the polymerizable functional group, and having a branched structure which is positionally and sterically symmetric and pure than the conventional ones.

It must be stated here that the present invention is not restricted to the embodiments shown by Examples. The embodiments shown by Examples are merely examples so that any embodiments composed of substantially the same technical concept as disclosed in the claims of the present invention and expressing a similar effect are included in the technical scope of the present invention.

INDUSTRIAL APPLICABILITY

According to the present invention, a symmetric hyperbranched silicone-modified polymerizable compound useful for a paint, an ophthalmic device composition, or a cosmetic composition including skin care, hair, an antiperspirant, a deodorant, makeup or ultraviolet protective, etc., and a modularized manufacturing method of the same are provided.

What is claimed is:

1. A symmetric hyperbranched silicone-modified polymerizable compound of formula (1), $$(R^A R^B)_2 CHOR^C_c R^D \quad (1)$$

wherein
  $R^A$ represents a monovalent linear, branched or cyclic siloxane chain;
  $R^B$ is a divalent hydrocarbonylene methylene ether group of the following formula
  —$CH_2 CR^{b1} R^{b2} (CR^{b3} R^{b4})_{n1} OCH_2$— that is arranged in formula (1) as follows $(R^A CH_2 CR^{b1} R^{b2} (CR^{b3} R^{b4})_{n1} OCH_2)_2 CHOR^C_c R^D$, wherein
  $R^{b1}$, $R^{b2}$, $R^{b3}$, and $R^{b4}$ each may be the same or different, and each represent a hydrogen atom or a linear, branched or cyclic hydrocarbon group having 1 to 10 carbon atoms, each of which may be bonded, "n1" represents an integer selected from 0 to 10, and when "n1" represents 1, $R^{b1}$ is a hydrocarbon group having 1 to 10 carbon atoms and $R^{b2}$ is a hydrogen atom;
  $R^C$ represents a divalent linking group;
  "c" represents 0 or 1; and
  $R^D$ represents an unsaturated polymerizable functional group.

2. The symmetric hyperbranched silicone-modified polymerizable compound according to claim 1, wherein "n1" represents an integer selected from 1 to 10.

3. The symmetric hyperbranched silicone-modified polymerizable compound according to claim 1, wherein
  $R^C$ is a linking group selected from the group consisting of
  —$XR^Y_y R^Z O$—,
  —$XR^Y_y CR^{Z'} R^{Z''} O$—, and
  an oligoalkyleneoxy group, the oligoalkyleneoxy group having 1 to 10 repeating units, where the repeating unit includes an alkylene group having 2 to 10 carbon atoms;
  wherein
  X represents a group selected from —$CH_2$—, —$C(=O)$—, and —$C(=S)$—
  $R^Y$ represents a divalent functional group containing 1 atom selected from nitrogen atom, oxygen atom, sulfur atom, and carbon atom,
  $R^Z$ represents a linear, branched or cyclic alkylene group having 2 to 10 carbon atoms which may be substituted by oxygen atom,
  "y" represents an integer selected from 0 or 1, and
  $R^{Z'}$ and $R^{Z''}$ each represent an alkyl group having 1 to 10 carbon atoms.

4. The symmetric hyperbranched silicone-modified polymerizable compound according to claim 2, wherein
  $R^C$ is a linking group selected from the group consisting of
  —$XR^Y_y R^Z O$—,
  —$XR^Y_y CR^{Z'} R^{Z''} O$—, and
  an oligoalkyleneoxy group, the oligoalkyleneoxy group having 1 to 10 repeating units, where the repeating unit includes an alkylene group having 2 to 10 carbon atoms;
  wherein
  X represents a group selected from —$CH^2$—, —$C(=O)$—, and —$C(=S)$—,
  $R^y$ represents a divalent functional group containing 1 atom selected from nitrogen atom, oxygen atom, sulfur atom, and carbon atom,
  $R^Z$ represents a linear, branched or cyclic alkylene group having 2 to 10 carbon atoms which may be substituted by oxygen atom,
  "y" represents an integer selected from 0 or 1, and
  $R^{Z'}$ and $R^{Z''}$ each represent an alkyl group having 1 to 10 carbon atoms.

5. A modularized manufacturing method for preparing the symmetric hyperbranched silicone-modified polymerizable compound of claim 1, wherein
  the compound of formula (1) is manufactured by reacting an intermediate of the general formula (2) and a compound having an unsaturated polymerizable functional group, $$(R^A R^B)_2 CHOH \quad (2)$$

wherein
  $R^A$ has the same meaning as defined above, and
  $R^B$ is a divalent hydrocarbonylene methylene ether group of the following formula —$CH_2CR^{b1}R^{b2}(CR^{b3}R^{b4})_{n1}OCH_2$— that is arranged in general formula (2) as follows $(R^A CH_2 CR^{b1} R^{b2} (CR^{b3} R^{b4})_{n1} OCH_2)_2 CHOH$.

6. The modularized manufacturing method according to claim 5, further comprising preparing the intermediate of the general formula (2) by subjecting a compound of formula (3) and a compound of formula (4) to hydrosilylation reaction, $$R^{A'} \quad (3)$$

wherein $R^{A'}$ represents a linear, branched or cyclic siloxane having one reactive hydrogen in the molecule, $$R^{B'}{}_2 CHOH \quad (4)$$

wherein $R^{B'}$ represents a monovalent hydrocarbonylene methylene ether group represented by $CH_2$=$CR^{b1}(CR^{b3}R^{b4})_{n1}OCH_2$— which has a double bond at the terminal, $R^{b1}$, $R^{h3}$ and $R^{b4}$ have the same meanings as defined above, and "n1" represents an integer selected from 0 to 10, and when "n1'" represents 1, $R^{b1}$ is a hydrocarbon group having 1 to 10 carbon atoms and $R^{b2}$ is a hydrogen atom.

7. The modularized manufacturing method according to claim 6, wherein "n1'" represents an integer selected from 1 to 10.

8. The modularized manufacturing method according to claim 6, wherein transition metal catalyst and radical scavenger are used in the hydrosilylation reaction.

9. The modularized manufacturing method according to claim 7, wherein transition metal catalyst and radical scavenger are used in the hydrosilylation reaction.

10. The modularized manufacturing method according to claim 8, wherein the transition metal catalyst is platinum catalyst.

11. The modularized manufacturing method according to claim 9, wherein the transition metal catalyst is platinum catalyst.

12. The modularized manufacturing method according to of claim 5, wherein a compound of formula (5) or a compound of formula (6) is used as the compound having an unsaturated polymerizable functional group, and reacted by using the intermediate of the general formula (2) and catalyst, $$R^{D'} \quad (5)$$

wherein $R^{D'}$ represents an unsaturated polymerizable compound having a reactive functional group, $$R^{C'}R^{D} \quad (6)$$

wherein $R^D$ has the same meaning as defined above, and $R^{C'}$ represents a monovalent reactive group.

13. The modularized manufacturing method according to claim 12, wherein $R^{C'}$ is a monovalent reactive group selected from the group consisting of
X=$R^Y R^Z O$—,
T-X—$R^Y{}_y R^Z O$—,
X=$R^Y CR^{Z'} R^{Z''} O$—,
T-X—$R^Y{}_y CR^{Z'} R^{Z''} O$—, and
an oligoalkyleneoxy group having a reactive group at one terminal thereof, the oligoalkyleneoxy group having 1 to 10 repeating units, where the repeating unit includes an alkylene group having 2 to 10 carbon atoms;
wherein
X, $R^Y$, $R^Z$, "y", $R^{Z'}$ and $R^{Z''}$ have the same meanings as defined above,
$R^Y$ represents a trivalent functional group containing 1 atom selected from nitrogen atom, oxygen atom, sulfur atom, and carbon atom, and T represents a hydroxyl group, or an atom selected from chlorine atom and bromine atom.

14. The modularized manufacturing method according to claim 12, wherein $R^{D'}$ is an unsaturated polymerizable compound obtained by bonding an unsaturated group with a reactive functional group directly or through a linking group in the molecule, wherein
the unsaturated group is selected from the group consisting of
acrylic group,
methacrylic group,
alkynyl group,
styryl group,
indenyl group,
alkenyl group,
cycloalkenyl group,
norbornyl group,
conjugated alkadiene group,
non-conjugated alkadiene group, and
vinyl ether group,
where each unsaturated group may contain a linear, branched or cyclic substituent having 1 to 10 carbon atoms and contain hetero atom(s), and
the reactive functional group is selected from the group consisting of
hydroxyl group,
amino group,
hydroxycarbonyl group,
aldehyde group,
acid halide group,
ester group,
haloformate group,
halogenated alkyl group,
isocyanate group,
isothiocyanate group,
ketene group,
phosphate group,
epoxy group,
aziridine group,
tosyl group,
mesyl group,
trifluoromethanesulfonyl group,
bromane group,
iodane group,
halogenated aryl group, and
nitroaryl group.

15. The modularized manufacturing method according to claim 13, wherein $R^{D'}$ is an unsaturated polymerizable compound obtained by bonding an unsaturated group with a reactive functional group directly or through a linking group in the molecule, wherein
the unsaturated group is selected from the group consisting of
acrylic group,
methacrylic group,
alkynyl group,
styryl group,
indenyl group,
alkenyl group,
cycloalkenyl group,
norbornyl group,
conjugated alkadiene group,
non-conjugated alkadiene group, and
vinyl ether group,
where each unsaturated group may contain a linear, branched or cyclic substituent having 1 to 10 carbon atoms and contain hetero atom(s), and the reactive functional group is selected from the group
consisting of
hydroxyl group,
amino group,
hydroxycarbonyl group,
aldehyde group,
acid halide group,
ester group,
haloformate group,
halogenated alkyl group,
isocyanate group,
isothiocyanate group,
ketene group,
phosphate group,
epoxy group,
aziridine group,
tosyl group,
mesyl group,
trifluoromethanesulfonyl group,
bromane group,
iodane group,
halogenated aryl group, and
nitroaryl group.

16. The modularized manufacturing method according to claim 12, wherein $R^D$ is a monovalent unsaturated polymerizable functional group selected from the group consisting of
acrylic group,
methacrylic group,
alkynyl group,
styryl group,
indenyl group,
alkenyl group,
cycloalkenyl group,
norbornyl group,
conjugated alkadiene group,
non-conjugated alkadiene group, and
vinyl ether group,
where each monovalent unsaturated polymerizable functional group may contain a linear, branched or cyclic substituent having 1 to 10 carbon atoms and contain hetero atom(s).

17. The modularized manufacturing method according to claim 13, wherein $R^D$ is a monovalent unsaturated polymerizable functional group selected from the group consisting of
acrylic group,
methacrylic group,
alkynyl group,
styryl group,
indenyl group,
alkenyl group,
cycloalkenyl group,
norbornyl group, conjugated alkadiene group,
non-conjugated alkadiene group, and
vinyl ether group,
where each monovalent unsaturated polymerizable functional group may contain a linear, branched or cyclic substituent having 1 to 10 carbon atoms and contain hetero atom(s).

18. The modularized manufacturing method according to claim 12, wherein
the catalyst for reacting the intermediate of the general formula (2) and the compound having an unsaturated polymerizable functional group is used in an amount of 0.001 to 0.500 mol % based on the amount of the intermediate of the general formula (2), and
the catalyst is either
a tertiary organic base; or
one or more Lewis acids selected from the group consisting of organic Lewis acids, inorganic Lewis acids, tin complex Lewis acids, titanium complex Lewis acids, iron complex Lewis acids, copper complex Lewis acids, zinc complex Lewis acids, aluminum complex Lewis acids, zirconium complex Lewis acids, yttrium complex Lewis acids, scandium complex Lewis acids, indium complex Lewis acids, lanthanum complex Lewis acids, cerium complex Lewis acids, samarium complex Lewis acids, europium complex Lewis acids, and silicon complex Lewis acids.

* * * * *